Figure 2A:
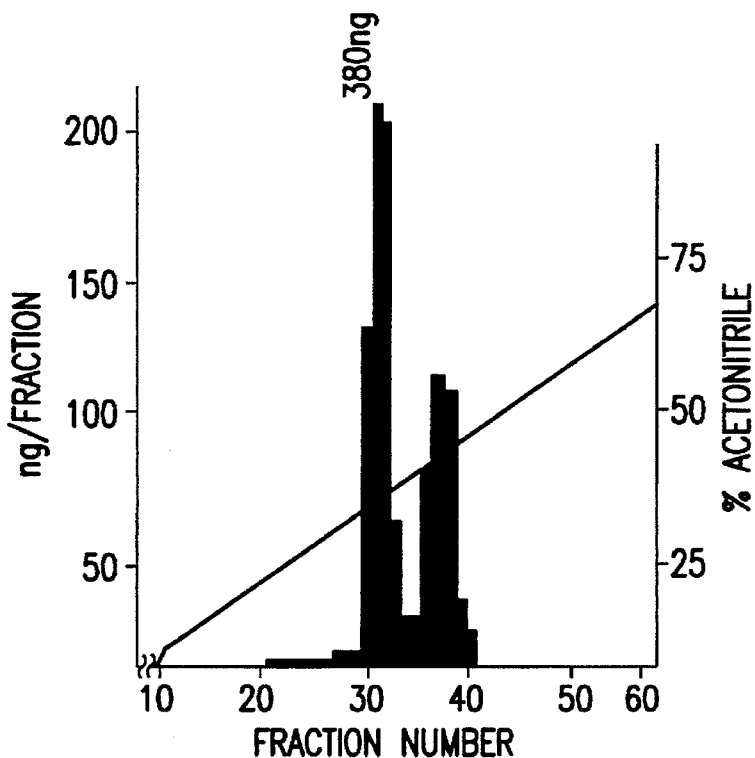

United States Patent [19]
Zohar et al.

[11] Patent Number: 5,643,877
[45] Date of Patent: Jul. 1, 1997

[54] COMPOUNDS COMPRISING GONADOTROPIN RELEASING HORMONE (GNRH) AND METHODS FOR CONTROLLING REPRODUCTION IN FISH

[75] Inventors: Yonathan Zohar, Baltimore, Md.; Nancy M. Sherwood, Victoria, Canada; Jean Rivier, LaJolla, Calif.; Jim Powell, Victoria, Canada; Yoav Gothilf, Baltimore, Md.

[73] Assignees: University of Maryland Biotechnology Institute, College Park, Md.; University of Victoria Innovation and Development Corporation, British Columbia, Canada

[21] Appl. No.: 341,219

[22] Filed: Dec. 5, 1994

[51] Int. Cl.$^6$ .............................. A61K 38/09; C07K 7/23
[52] U.S. Cl. ............................ 514/15; 514/800; 530/313; 930/20; 930/21; 930/130
[58] Field of Search ........................... 514/2, 8, 15, 21, 514/800; 530/313, 328, 324; 930/20, 21, 130

[56] References Cited

U.S. PATENT DOCUMENTS

| | | | |
|---|---|---|---|
| 4,410,514 | 10/1983 | Vale, Jr. et al. | 424/177 |
| 4,443,368 | 4/1984 | Sherwood et al. | 260/112.5 |
| 4,758,552 | 7/1988 | Gulyás et al. | 514/15 |
| 5,076,208 | 12/1991 | Zohar et al. | 119/2 |
| 5,093,246 | 3/1992 | Cech et al. | 435/91 |
| 5,288,705 | 2/1994 | Zohar | 514/15 |

FOREIGN PATENT DOCUMENTS

| | | |
|---|---|---|
| 80-40210 | 10/1980 | Japan . |
| 2 152 342 | 8/1985 | United Kingdom . |

OTHER PUBLICATIONS

Adelman et al. "Isolation of the gene and hypothalamic cDNA for the common precursor of gonadotropin–releasing hormone and prolactin release–inhibiting factor in human and rat." *Proc. Natl. Acad. Sci. USA* 83: 179–183 (1986).

Alestrom et al. "Fish gonadotropin–releasing hormone gene and molecular approaches for control of sexual maturation: Development of a transgenic fish model." *Mol. Marine Biol. and Biotech.* 1(4/5): 376–379 (1992).

Amoss et al. "Purification, amino acid composition and N–terminus of the hypothalamic luteinizing hormone releasing factor (LFR) of ovine origin". *Biochem. Biophys. Res. Commun.* 44: 205–210 (1971).

Ashihara et al. Sequence listing copied from a poster which appeared at the IUBS Symposium on "Advances in the Molecular Endocrinology of Fish," May 23–25, 1993, Toronto, Canada. Copy of poster is unavailable; Abstract P4, (1994).

Ausubel et al. (Eds.) *Current Protocols in Molecular Biology*, vols. I & II, Green Publishing Associates, Inc. and John Wiley & Sons, Inc., New York, 1989.

Okuzawa et al. Gen. Compar. Endocrinol. 96(2):234–42, 1994.

Bogerd et al. "Isolation, characterization and epxression of cDNAs encoding the catfish–type and chicken–II–type gonadotropin–releasing–hormone precursors in the African catfish." *Eur. J. Biochem.* 222(2): 541–549 (1994).

Bond et al. "Characterization of complementary DNA encoding the precursor for gonadotropin–releasing hormone and its associated peptide from a teleost fish". *Mol. Endocrinol.* 5: 931–937 (1991).

Chen et al. "Transgenic fish". *Tibtech* 8: 209–215 (1990).

Conlon et al. "Two molecular forms of gonadotropin–releasing hormone from the brain of the frog, *Rana ridibunda*: Purification, characterization, and distribution". *Endocrinol.* 132: 2117–2123 (1993).

Copeland et al. "Luteinizing hormone–releasing hormone: Sequential versus conformational specificity of antiluteinizing hormone–releasing hormone sera". *Endocrinology* 104: 1504–1512 (1979).

Dunn et al. "Characterization of the chicken preprogonadotrophin–releasing hormone–I gene". *J. Mol. Endocrinol.* 11: 19–29 (1983).

Hayes et al. "The frog gonadotropin–releasing hormone–I (GnRH–I) gene has a mammalian–like expression pattern and conserved domains in GnRH–associated peptide, but brain onset is delayed until metamorphosis". *Endocrinol.* 134(4): 1835–1845 (1984).

Kelsall et al. "Phylogeny and ontogeny of gonadotropin–releasing hormone: Comparison of guinea pig, rat, and a protochordate". *Gen. Comp. Endocrinol.* 78:479–494 (1990).

King et al. "Structure of chicken hypothalamic luteinizing hormone releasing hormone". *J. Biol. Chem.* 257: 10729–10732 (1982).

King et al. "Chromatographic and immunological evidence for mammalian GnRH and chicken GnRH II in eel (*Anguilla anguilla*) brain and pituitary". *Peptides* 11: 507–514 (1990).

Klungland et al. "The Atlantic salmon prepro–gonadotropin releasing hormone gene and mRNA". *Mol. and Cell. Endocrinol.* 84: 167–174 (1992).

Kozak. "Possible role of flanking nucleotides in recognition of the AUG initiator codon by eukaryotic ribosomes". *Nucl. Acids Res.* 9: 5233–5252 (1981).

Lin et al. "Effects of [D–Ala$^6$, Pro$^9$–NEt]–LHRH and catecholaminergic drugs on gonadotropin secretion and ovulation in the Chinese Loach (*Paramisgurnus dabryanus*)." *Gen. Comp. Endocrinol.* 64: 389–395 (1986).

Lovejoy et al. "Distinct sequence of gonadotropin–releasing hormone (GnRH) in dogfish brain provides insight into GnRH evolution". *Proc. Natl. Acad. Sci. USA* 89: 6373–6377 (1992).

Mason et al. "The hypogonadal mouse: Reproductive functions restored by gene therapy". *Science* 234: 1372–1378 (1986).

Matsuo et al. "Structure of the porcine LH– and FSH–releasing hormone. I. The proposed amino acid sequence". *Biochem. Biophys. Res. Commun.* 43: 1334–1339 (1971).

Miyamoto et al. "Identification of the second gonadotropin–releasing hormone in chicken hypothalamus: Evidence that gonadotropin secretion is probably controlled by two distinct gonadotropin–releasing hormones in avian species". *Proc. Natl. Acad. Sci. USA* 81: 3875–3878 (1984).

Ngamvongchon et al. "Primary structures of two forms of gonadotropin–releasing hormone, one distinct and one conserved, from catfish brain." *Mol. Cell. Neurosci.* 3: 17–22 (1992).

Peter et al. "Gonadotropin release from the pars distalis of goldfish, Carassius auratus, transplanted beside the brain or into the brain ventricles: Additional evidence for gonadotropin–release–inhibitory factor". Gen. Comp. Endocrinol. 55: 337–346 (1984).

Peter et al. "Induced ovulation and spawning of cultured freshwater fish in China: Advances in application of GnRH analogues and dopamine antagonists". Aquaculture 74: 1–10 (1988).

Rivier et al. "Reversed–phase high–performance liquid chromatography: Preparative purification of synthetic peptides". J. Chromatog. 288: 303–328 (1984).

Rivier et al. "Gonadotropin–releasing hormone antagonists with $N^\omega$–Triazolylornithine, –lysine, or –p–aminophenylalanine residues at positions 5 and 6". J. Med. Chem. 35: 4270–4278 (1992).

Sambrook et al. Molecular Cloning: A Laboratory Manual, Cold Spring Harbor Laboratories Press, Cold Spring Harbor, NY, 1989; (cover pages provided).

Schally et al. "Isolation and properties of the fish and LH–releasing hormone". Biochem. Biophys. Res. Commun. 43: 393–399 (1971).

Seeburg & Adelman. "Characterization of cDNA for precursor of human luteinizing hormone releasing hormone". Nature 311: 666–668 (1984).

Sherwood et al. "Characterization of a teleost gonadotropin–releasing hormone". Proc. Natl. Acad. Sci. USA 80: 2794–2798 (1983).

Sherwood et al. "Primary structure of a gonadotropin–releasing hormone from Lamprey brain". J. Biol. Chem. 261: 4812–4819 (1986).

Sherwood et al. "Gonadotropin–releasing hormone (GnRH) in bony fish that are phylogenetically ancient: Reedfish (Calamoichthys calabaricus), sturgeon (Acipenser transmontanus), and alligator gar (Lepisosteus spatula)." Gen. Comp. Endocrinol. 84: 44–57 (1991).

Sherwood et al. "Gonadotropin–releasing hormones, including a novel form, in snook Centropomus undecimalis, in comparison with forms in black sea bass Centropristis striata". Regul. Pept. 46: 523–534 (1993).

Sower et al. "Primary structure and biological activity of a third gonadotropin–releasing hormone from Lamprey brain". Endocrinol. 132: 1125–1131 (1993).

Stacey et al. "Ovulatory surge of gonadotropin in the goldfish, Carassius auratus". Gen. Comp. Endocrinol. 37: 246–249 (1979).

Suzuki et al. "Characterization and localization of mRNA encoding the salmon–type gonadotrophin–releasing hormone precursor of the masu salmon". J. Mol. Endocrin. 9: 73–82 (1992).

Wetsel et al. "Metabolism of pro–luteinizing hormone–releasing hormone in immortalized hypothalamic neurons". Endocrinology 129: 1584–1595 (1991).

White et al. "A second gene for gonadotropin–releasing hormone: cDNA and expression pattern in the brain". Proc. Natl. Acad. Sci. USA 91: 1423–1427 (1994).

Zohar et al. "Spawning kinetics in the gilthead sea–bream, Sparus aurata L. after low doses of human chronic gonadotropin". J. Fish Biol. 15: 665–670 (1979).

Zohar et al. "Short–term profiles of plasma gonadotropin and $17\alpha$–hydroxy, 20+62 –dihydroprogesterone levels in the female rainbow trout at the periovulatory period". Gen. Comp. Endocrinol. 64: 189–198 (1986).

Zohar et al. "Gonadotropin Biodynamics Following GnRH administration oin the gilthead seabream, Sparus aurata: a combined radioimminoassay (RIA) and immunocytochemical (ICC) study"; In: Proceedings of the 3rd Intl. Symp. on Reprod. Physiol. of Fish; St. John's, Newfoundland, Canada; Aug. 1987; pp. 46 & 106.

Zohar et al. "Development of a homologous radioimmunoassay for a gonadotropin of the gilthead seabream, Sparus aurata". Aquaculture 88: 189–204 (1990).

Primary Examiner—Vasu Jagannathan
Assistant Examiner—Christine Saoud
Attorney, Agent, or Firm—Pennie & Edmonds

[57] ABSTRACT

Novel peptide hormones which influence the release of gonadotropins by the pituitary gland in fish are disclosed. Methods in which such peptides may be administered to fish to control their reproduction are also described. Furthermore, novel isolated cDNA encoding the precursor of the novel gonadotropin-releasing hormone is disclosed. The use of such cDNA in controlling the gonadal development and spawning of fish is also described.

19 Claims, 9 Drawing Sheets

|  | 1 | 2 | 3 | 4 | 5 | 6 | 7 | 8 | 9 | 10 |
|---|---|---|---|---|---|---|---|---|---|---|
| Seabream GnRH | pGlu | His | Trp | Ser | Tyr | Gly | Leu | Ser | Pro | Gly-NH₂ |
| Mammalian GnRH | pGlu | His | Trp | Ser | Tyr | Gly | Leu | Arg | Pro | Gly-NH₂ |
| Chicken GnRH-I | pGlu | His | Trp | Ser | Tyr | Gly | Leu | Gln | Pro | Gly-NH₂ |
| Catfish GnRH | pGlu | His | Trp | Ser | His | Gly | Leu | Asn | Pro | Gly-NH₂ |
| Salmon GnRH | pGlu | His | Trp | Ser | Tyr | Gly | Trp | Leu | Pro | Gly-NH₂ |
| Dogfish GnRH | pGlu | His | Trp | Ser | His | Gly | Trp | Leu | Pro | Gly-NH₂ |
| Chicken GnRH-II | pGlu | His | Trp | Ser | His | Gly | Trp | Tyr | Pro | Gly-NH₂ |
| Lamprey GnRH-III | pGlu | His | Trp | Ser | His | Asp | Trp | Lys | Pro | Gly-NH₂ |
| Lamprey GnRH-I | pGlu | His | Tyr | Ser | Leu | Glu | Trp | Lys | Pro | Gly-NH₂ |

FIG.1

```
           1   2   3   4   5   6   7   8   9  10  11  12  13
Pre-sbGnRH: Gln-His-Trp-Ser-Tyr-Gly-Leu-Ser-Pro-Gly-Gly-Lys-Arg

5'Primers
1-8 I:      CAG CAT TGG TCI TAT GGI TTN TC
                        C               C
1-8 II:     CAG CAT TGG TCI TAT GGI TTN AG
                        C               C
Internal probe:                 TCN CCT GGI GGI AAA CG
                                AG              G   A
```

FIG.7 cDNA ENCODING FOR THE SEABREAM GnRH PRECURSOR

```
                              -25              -20
                               M  A  P  Q  T  S  N
CGGCACGAGCAGCGAGAAAACACCTGAGCAAGAAGAATGGCTCCACAGACCTCAAA    55
                   -10
   L  W  I  L  L  L  V  V  V  M  M  M  S  Q  G  C  C
CCTCTGGATCCTGCTGCTGCTGGTGGTGGTGATGATGATGTCACAGGGCTGCTGTC   110
1                           10
  Q  H  W  S  Y  G  L  S  P  G  G  K  R  D  L  D  S  L  S
AGCACTGGTCGTATGGACTGAGTCCAGGAGGGAAGCGGGACCTGGACAGCCTCTCG   165
     20                          30
  D  T  L  G  N  I  I  E  R  F  P  H  V  D  S  P  C  S  V
GACACGCTCGGCAACATTATCGAGCGTTTTCCTCACGTCGACTCTCCCTGCAGTGT   220
         40                          50
     L  G  C  V  E  E  P  H  V  P  R  M  Y  R  M  K  G  F
TCTGGGCTGTGTCGAGGAGCCACATGTCCCCAGAATGTACAGAATGAAAGGATTTA   275
            60                          70
  I  G  S  E  R  D  I  G  H  R  M  Y  K  K  *  *
TTGGCAGCGAGCGGGACATCGGACACAGAATGTACAAGAAATGATGATTATCTGAA   330
TTTACAATAAATGATTATATTAGCAAn                                356
```

FIG.8

FIG. 9

|  | Signal Peptide | | GnRH | GnRH Associated Peptide (GAP) |
|---|---|---|---|---|
| sbGnRH | MAPQTSNLWILLLVVMMMSQCCC | | QHWSYGLSPGGKR | DLDSLSDTL-GNIIERFPHVDSPCSVLGQVEEPHVERMYRMKGFIIGS—ERDIGHRMYKK |
| Mouse | M ILKLMAGILLLTVCLEGCSSS | | QHWSYGLRPGGKR | NTEHLVESFQEMGKEVDQMAEPQH—FEQTVHWPRSPLRDLRGALESLIEEEARQKKM |
| Frog | MK AFPTFALLFLVLLF SAHVSDA | | QHWSYGLRPGGKR | DTESLQDMYHEITPMEVALFPELER—LEQSV-PQSRLNVLRGALMNWLEGENRKKI |
| cGnRH-I | MEK SRKILVGVLLE TASAAICLA | | QHWSYGLQPGGKR | NAENLVESFQEIANEMESLGEGQK—AEQPGSYQHPRLSDLKETMASLIEGEARRKEI |
| cGnRH-II | M CVSRLALLGLLLCVGAQLSFA | | QHWSHGWYPGGKR | ELDSFG—TSEISEEIK——LCEAGECSYLRPQ-RRSILRNILLDALARELQKRK |
| cfGnRH | M GIKRALWMMVVCWVL QVSA | | QHWSHGLNPGGKR | AV——MQESAEEIPRSSGYLC————DYVAVSPRNKPFRLKDLLITPVAGREIEE |
| sGnRH | ME AGSRVIMVLLLALVV QVTLS | | QHWSYGWLPGGKR | SVGELEATIR——MMGTGGVVSLPDEANAQIQERIRPYNIINDDSSHFDRKKRFPNN |

Hydrophobic Core / Polar-nonpolar

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 362 base pairs
( B ) TYPE: nucleic acid
( C ) STRANDEDNESS: double
( D ) TOPOLOGY: unknown ( i i ) MOLECULE TYPE: cDNA ( i x ) FEATURE:
( A ) NAME/KEY: CDS
( B ) LOCATION: 37..321

( i x ) FEATURE:
( A ) NAME/KEY: mat_peptide
( B ) LOCATION: 112..321

( x i ) SEQUENCE DESCRIPTION: SEQ ID NO:1:

```
CGGCACGAGC  AGCGAGAAAA  CACCTGAGCA  AGAAGA ATG GCT CCA CAG ACC TCA        54
                                           Met Ala Pro Gln Thr Ser
                                           -25                 -20
```

```
AAC  CTC  TGG  ATC  CTG  CTG  CTG  GTG  GTG  GTG  ATG  ATG  ATG  TCA  CAG         102
Asn  Leu  Trp  Ile  Leu  Leu  Leu  Val  Val  Val  Met  Met  Met  Ser  Gln
              -15                 -10                          -5

GGC  TGC  TGT  CAG  CAC  TGG  TCG  TAT  GGA  CTG  AGT  CCA  GGA  GGG  AAG  CGG    150
Gly  Cys  Cys  Gln  His  Trp  Ser  Tyr  Gly  Leu  Ser  Pro  Gly  Gly  Lys  Arg
                1              5                         10

GAC  CTG  GAC  AGC  CTC  TCG  GAC  ACG  CTC  GGC  AAC  ATT  ATC  GAG  CGT  TTT    198
Asp  Leu  Asp  Ser  Leu  Ser  Asp  Thr  Leu  Gly  Asn  Ile  Ile  Glu  Arg  Phe
          15                        20                     25

CCT  CAC  GTC  GAC  TCT  CCC  TGC  AGT  GTT  CTG  GGC  TGT  GTC  GAG  GAG  CCA    246
Pro  His  Val  Asp  Ser  Pro  Cys  Ser  Val  Leu  Gly  Cys  Val  Glu  Glu  Pro
 30                       35                      40                       45

CAT  GTC  CCC  AGA  ATG  TAC  AGA  ATG  AAA  GGA  TTT  ATT  GGC  AGC  GAG  CGG    294
His  Val  Pro  Arg  Met  Tyr  Arg  Met  Lys  Gly  Phe  Ile  Gly  Ser  Glu  Arg
                     50                       55                      60

GAC  ATC  GGA  CAC  AGA  ATG  TAC  AAG  AAA  TGATGATTAT  CTGAATTTAC              341
Asp  Ile  Gly  His  Arg  Met  Tyr  Lys  Lys
                65                       70

AATAAATGAT  TATATTAGCA  A                                                        362

( 2 ) INFORMATION FOR SEQ ID NO:2:

( i ) SEQUENCE CHARACTERISTICS:
                ( A ) LENGTH: 95 amino acids
                ( B ) TYPE: amino acid
                ( D ) TOPOLOGY: linear ( i i ) MOLECULE TYPE: protein ( x i ) SEQUENCE DESCRIPTION: SEQ ID NO:2:

Met  Ala  Pro  Gln  Thr  Ser  Asn  Leu  Trp  Ile  Leu  Leu  Leu  Val  Val
-25                      -20                     -15                      -10

Val  Met  Met  Met  Ser  Gln  Gly  Cys  Cys  Gln  His  Trp  Ser  Tyr  Gly  Leu
               -5                      1                        5

Ser  Pro  Gly  Gly  Lys  Arg  Asp  Leu  Asp  Ser  Leu  Ser  Asp  Thr  Leu  Gly
          10                        15                        20

Asn  Ile  Ile  Glu  Arg  Phe  Pro  His  Val  Asp  Ser  Pro  Cys  Ser  Val  Leu
          25                        30                        35

Gly  Cys  Val  Glu  Glu  Pro  His  Val  Pro  Arg  Met  Tyr  Arg  Met  Lys  Gly
 40                       45                        50                       55

Phe  Ile  Gly  Ser  Glu  Arg  Asp  Ile  Gly  His  Arg  Met  Tyr  Lys  Lys
               60                        65                        70
```

( 2 ) INFORMATION FOR SEQ ID NO:3:

( i ) SEQUENCE CHARACTERISTICS:
                ( A ) LENGTH: 10 amino acids
                ( B ) TYPE: amino acid
                ( C ) STRANDEDNESS: single
                ( D ) TOPOLOGY: unknown ( i i ) MOLECULE TYPE: peptide ( i x ) FEATURE:
                ( A ) NAME/KEY: Modified-site
                ( B ) LOCATION: 1
                ( D ) OTHER INFORMATION: /label=Xaa
                    / note= "Xaa at position 1 = Pyroglutamic Acid"

( i x ) FEATURE:
                ( A ) NAME/KEY: Active-site
                ( B ) LOCATION: 10
                ( D ) OTHER INFORMATION: /label=Xaa
                    / note= "Xaa at position 10 = amidated Glycine,
                    wherein an amino group replaces the hydroxyl portion of the carboxyl group."

( x i ) SEQUENCE DESCRIPTION: SEQ ID NO:3:

Xaa His Trp Ser Tyr Gly Leu Ser Pro Xaa
1              5                    10

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:4:

Gln His Trp Ser Tyr Gly Leu Ser Pro Gly Gly Lys Arg
1              5                    10

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: unknown ( i i ) MOLECULE TYPE: DNA ( i x ) FEATURE:
        ( A ) NAME/KEY: misc_feature
        ( B ) LOCATION: 1..23
        ( D ) OTHER INFORMATION: /label=H
            / note= "H=Inosine"

( x i ) SEQUENCE DESCRIPTION: SEQ ID NO:5:

CAGCA Y TGGT CHTATGGH Y T NTC        23

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: unknown ( i i ) MOLECULE TYPE: DNA ( i x ) FEATURE:
        ( A ) NAME/KEY: modified_base
        ( B ) LOCATION: 12
        ( D ) OTHER INFORMATION: /label=H
            / note= "H=Inosine"

( i x ) FEATURE:
        ( A ) NAME/KEY: modified_base
        ( B ) LOCATION: 18
        ( D ) OTHER INFORMATION: /mod_base=OTHER
            / label= H
            / note= "H=Inosine"

( x i ) SEQUENCE DESCRIPTION: SEQ ID NO:6:

CAGCA Y TGGT CHTATGGH Y T NAG        23

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: unknown (i i) MOLECULE TYPE: DNA (i x) FEATURE:
    (A) NAME/KEY: misc_feature
    (B) LOCATION: 1..17
    (D) OTHER INFORMATION: /label=H
        / note= "H=Inosine"

(x i) SEQUENCE DESCRIPTION: SEQ ID NO:7:

WSNCCTGGHG GHAARMG 17

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:8:

His Trp Ser Tyr Gly Leu Ser Pro Gly
    1               5

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:9:

His Trp Ser His Gly Trp Tyr Pro Gly
    1               5

(2) INFORMATION FOR SEQ ID NO:10:

(i) SEQUENCE CHARACTERISTICS:
        (A) LENGTH: 10 amino acids
        (B) TYPE: amino acid
        (C) STRANDEDNESS: single
        (D) TOPOLOGY: unknown (i i) MOLECULE TYPE: peptide (i x) FEATURE:
        (A) NAME/KEY: Modified-site
        (B) LOCATION: 1
        (D) OTHER INFORMATION: /note= "Xaa = pGlu
            (pyroglutamic acid)"

(i x) FEATURE:
        (A) NAME/KEY: Modified-site
        (B) LOCATION: 6
        (D) OTHER INFORMATION: /note= "Xaa = a D-isomer of
            Trp, Ala, Phe, Lys, Pro, Met, Leu, Glu, Asn,
            Arg, Tyr, Cys, His, 2-cyclohexyl Gly, Nva,
            Orn, Thr, Abu, Phg, Ile, Glu, Asp, Nle or Val"

(i x) FEATURE:
        (A) NAME/KEY: Modified-site
        (B) LOCATION: 8
        (D) OTHER INFORMATION: /note= "Xaa = Ser, Ala, Thr,
            Pro, or Gly"

(i x) FEATURE:
        (A) NAME/KEY: Modified-site
        (B) LOCATION: 10
        (D) OTHER INFORMATION: /note= "Xaa may not exist;

peptide has carboxy terminal structure:

$$-\overset{O}{\underset{\|}{C}}-NHR$$, where R=H or C-nY-2nCY-3, and where
Y=H or F and n=0,1,2 or 3, provided that where
Xaa does not exist, n is not 0"

( x i ) SEQUENCE DESCRIPTION: SEQ ID NO:10:

```
Xaa His Trp Ser Tyr Xaa Leu Xaa Pro Xaa
1               5                   10
```

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: unknown ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="OTHER"
            / label= Glu1
            / note= "=pyroglutamic acid"

( i x ) FEATURE:
        ( A ) NAME/KEY: Modified-site
        ( B ) LOCATION: 10
        ( D ) OTHER INFORMATION: /product="OTHER"
            / label= Gly10
            / note= "amidated"

( x i ) SEQUENCE DESCRIPTION: SEQ ID NO:11:

```
Glu His Trp Ser Tyr Gly Leu Arg Pro Gly
1               5                   10
```

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: unknown ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="OTHER"
            / label= Glu1
            / note= "=pyroglutamic acid"

( i x ) FEATURE:
        ( A ) NAME/KEY: Modified-site
        ( B ) LOCATION: 10
        ( D ) OTHER INFORMATION: /product="OTHER"
            / label= Gly10
            / note= "amidated"

( x i ) SEQUENCE DESCRIPTION: SEQ ID NO:12:

```
Glu His Trp Ser Tyr Gly Leu Gln Pro Gly
1               5                   10
```

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: unknown ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="OTHER"
            / label= Glu1
            / note= "=pyroglutamic acid"

( i x ) FEATURE:
        ( A ) NAME/KEY: Modified-site
        ( B ) LOCATION: 10
        ( D ) OTHER INFORMATION: /product="OTHER"
            / label= Gly10
            / note= "amidated"

( x i ) SEQUENCE DESCRIPTION: SEQ ID NO:13:

Glu  His  Trp  Ser  His  Gly  Leu  Asn  Pro  Gly
    1                      5                            10

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: unknown ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="OTHER"
            / label= Glu1
            / note= "=pyroglutamic acid"

( i x ) FEATURE:
        ( A ) NAME/KEY: Modified-site
        ( B ) LOCATION: 10
        ( D ) OTHER INFORMATION: /product="OTHER"
            / label= Gly10
            / note= "amidated"

( x i ) SEQUENCE DESCRIPTION: SEQ ID NO:14:

Glu  His  Trp  Ser  Tyr  Gly  Trp  Leu  Pro  Gly
    1                      5                            10

( 2 ) INFORMATION FOR SEQ ID NO:15:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: unknown ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 1
    ( D ) OTHER INFORMATION: /product="OTHER"
        / label= Glu1
        / note= "=pyroglutamic acid"

( i x ) FEATURE:
    ( A ) NAME/KEY: Modified-site
    ( B ) LOCATION: 10
    ( D ) OTHER INFORMATION: /product="OTHER"
        / label= Gly10
        / note= "amidated"

( x i ) SEQUENCE DESCRIPTION: SEQ ID NO:15:

Glu His Trp Ser His Gly Trp Leu Pro Gly
1               5                   10

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: unknown ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 1
    ( D ) OTHER INFORMATION: /product="OTHER"
        / label= Glu1
        / note= "=pyroglutamic acid"

( i x ) FEATURE:
    ( A ) NAME/KEY: Modified-site
    ( B ) LOCATION: 10
    ( D ) OTHER INFORMATION: /product="OTHER"
        / label= Gly10
        / note= "amidated"

( x i ) SEQUENCE DESCRIPTION: SEQ ID NO:16:

Glu His Trp Ser His Gly Trp Tyr Pro Gly
1               5                   10

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: unknown ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 1
    ( D ) OTHER INFORMATION: /product="OTHER"
        / label= Glu1
        / note= "=pyroglutamic acid"

( i x ) FEATURE:
    ( A ) NAME/KEY: Modified-site (B) LOCATION: 10
                (D) OTHER INFORMATION: /product="OTHER"
                    / label= Gly10
                    / note= "amidated"

(xi) SEQUENCE DESCRIPTION: SEQ ID NO:17:

Glu His Trp Ser His Asp Trp Lys Pro Gly
    1               5                   10

(2) INFORMATION FOR SEQ ID NO:18:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: unknown (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 1
        (D) OTHER INFORMATION: /product="OTHER"
            / label= Glu1
            / note= "=pyroglutamic acid"

(ix) FEATURE:
        (A) NAME/KEY: Modified-site
        (B) LOCATION: 10
        (D) OTHER INFORMATION: /product="OTHER"
            / label= Gly10
            / note= "amidated"

(xi) SEQUENCE DESCRIPTION: SEQ ID NO:18:

Glu His Tyr Ser Leu Glu Trp Lys Pro Gly
    1               5                   10

(2) INFORMATION FOR SEQ ID NO:19:

(i) SEQUENCE CHARACTERISTICS:
        (A) LENGTH: 90 amino acids
        (B) TYPE: amino acid
        (C) STRANDEDNESS: Not Relevant
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:19:

Met Ile Leu Lys Leu Met Ala Gly Ile Leu Leu Leu Thr Val Cys Leu
    1               5                   10                  15

Glu Gly Cys Ser Ser Gln His Trp Ser Tyr Gly Leu Arg Pro Gly Gly
                    20                  25                  30

Lys Arg Asn Thr Glu His Leu Val Glu Ser Phe Gln Glu Met Gly Lys
                35                  40                  45

Glu Val Asp Gln Met Ala Glu Pro Gln His Phe Glu Cys Thr Val His
            50                  55                  60

Trp Pro Arg Ser Pro Leu Arg Asp Leu Arg Gly Ala Leu Glu Ser Leu
    65                  70                  75                  80

Ile Glu Glu Glu Ala Arg Gln Lys Lys Met
                    85                  90

( 2 ) INFORMATION FOR SEQ ID NO:20:

( i ) SEQUENCE CHARACTERISTICS:
        ( A ) LENGTH: 89 amino acids
        ( B ) TYPE: amino acid
        ( C ) STRANDEDNESS: Not Relevant
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:20:

```
Met Lys Ala Phe Pro Thr Phe Ala Leu Leu Phe Leu Val Leu Leu Phe
 1               5                  10                  15
Ser Ala His Val Ser Asp Ala Gln His Trp Ser Tyr Gly Leu Arg Pro
             20                  25                  30
Gly Gly Lys Arg Asp Thr Glu Ser Leu Gln Asp Met Tyr His Glu Thr
         35                  40                  45
Pro Asn Glu Val Ala Leu Phe Pro Glu Leu Glu Arg Leu Glu Cys Ser
     50                  55                  60
Val Pro Gln Ser Arg Leu Asn Val Leu Arg Gly Ala Leu Met Asn Trp
 65                  70                  75                  80
Leu Glu Gly Glu Asn Arg Lys Lys Ile
                 85
```

( 2 ) INFORMATION FOR SEQ ID NO:21:

( i ) SEQUENCE CHARACTERISTICS:
        ( A ) LENGTH: 92 amino acids
        ( B ) TYPE: amino acid
        ( C ) STRANDEDNESS: Not Relevant
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:21:

```
Met Glu Lys Ser Arg Lys Ile Leu Val Gly Val Leu Leu Phe Thr Ala
 1               5                  10                  15
Ser Ala Ala Ile Cys Leu Ala Gln His Trp Ser Tyr Gly Leu Gln Pro
             20                  25                  30
Gly Gly Lys Arg Asn Ala Glu Asn Leu Val Glu Ser Phe Gln Glu Ile
         35                  40                  45
Ala Asn Glu Met Glu Ser Leu Gly Glu Gly Gln Lys Ala Glu Cys Pro
     50                  55                  60
Gly Ser Tyr Gln His Pro Arg Leu Ser Asp Leu Lys Glu Thr Met Ala
 65                  70                  75                  80
Ser Leu Ile Glu Gly Glu Ala Arg Arg Lys Glu Ile
                 85                  90
```

( 2 ) INFORMATION FOR SEQ ID NO:22:

( i ) SEQUENCE CHARACTERISTICS:
        ( A ) LENGTH: 85 amino acids
        ( B ) TYPE: amino acid
        ( C ) STRANDEDNESS: Not Relevant
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:22:

| Met | Cys | Val | Ser | Arg | Leu | Ala | Leu | Leu | Leu | Gly | Leu | Leu | Leu | Cys | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gly | Ala | Gln | Leu | Ser | Phe | Ala | Gln | His | Trp | Ser | His | Gly | Trp | Tyr | Pro |
|     |     |     | 20  |     |     |     |     | 25  |     |     |     | 30  |     |     |     |
| Gly | Gly | Lys | Arg | Glu | Leu | Asp | Ser | Phe | Gly | Thr | Ser | Glu | Ile | Ser | Glu |
|     |     | 35  |     |     |     |     | 40  |     |     |     |     | 45  |     |     |     |
| Glu | Ile | Lys | Leu | Cys | Glu | Ala | Gly | Glu | Cys | Ser | Tyr | Leu | Arg | Pro | Gln |
|     | 50  |     |     |     |     | 55  |     |     |     |     | 60  |     |     |     |     |
| Arg | Arg | Ser | Ile | Leu | Arg | Asn | Ile | Leu | Leu | Asp | Ala | Leu | Ala | Arg | Glu |
| 65  |     |     |     |     | 70  |     |     |     |     | 75  |     |     |     |     | 80  |
| Leu | Gln | Lys | Arg | Lys |     |     |     |     |     |     |     |     |     |     |     |
|     |     |     |     | 85  |     |     |     |     |     |     |     |     |     |     |     |

( 2 ) INFORMATION FOR SEQ ID NO:23:

( i ) SEQUENCE CHARACTERISTICS:
  ( A ) LENGTH: 80 amino acids
  ( B ) TYPE: amino acid
  ( C ) STRANDEDNESS: Not Relevant
  ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:23:

| Met | Gly | Ile | Lys | Arg | Ala | Leu | Trp | Trp | Met | Val | Cys | Val | Val | Val | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Leu | Gln | Val | Ser | Ala | Gln | His | Trp | Ser | His | Gly | Leu | Asn | Pro | Gly | Gly |
|     |     |     | 20  |     |     |     |     | 25  |     |     |     | 30  |     |     |     |
| Lys | Arg | Ala | Val | Met | Gln | Glu | Ser | Ala | Glu | Glu | Ile | Pro | Arg | Ser | Ser |
|     |     | 35  |     |     |     |     | 40  |     |     |     |     | 45  |     |     |     |
| Gly | Tyr | Leu | Cys | Asp | Tyr | Val | Ala | Val | Ser | Pro | Arg | Asn | Lys | Pro | Phe |
|     | 50  |     |     |     |     | 55  |     |     |     |     | 60  |     |     |     |     |
| Arg | Leu | Lys | Asp | Leu | Leu | Thr | Pro | Val | Ala | Gly | Arg | Glu | Ile | Glu | Glu |
| 65  |     |     |     |     | 70  |     |     |     |     | 75  |     |     |     |     | 80  |

( 2 ) INFORMATION FOR SEQ ID NO:24:

( i ) SEQUENCE CHARACTERISTICS:
  ( A ) LENGTH: 90 amino acids
  ( B ) TYPE: amino acid
  ( C ) STRANDEDNESS: Not Relevant
  ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:24:

| Met | Glu | Ala | Gly | Ser | Arg | Val | Ile | Met | Gln | Val | Leu | Leu | Leu | Ala | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Val | Val | Gln | Val | Thr | Leu | Ser | Gln | His | Trp | Ser | Tyr | Gly | Trp | Leu | Pro |
|     |     |     | 20  |     |     |     |     | 25  |     |     |     | 30  |     |     |     |
| Gly | Gly | Lys | Arg | Ser | Val | Gly | Glu | Leu | Glu | Ala | Thr | Ile | Arg | Met | Met |

|  | 35 |  |  |  | 40 |  |  |  |  | 45 |  |  |  |
|---|---|---|---|---|---|---|---|---|---|---|---|---|---|
| Gly | Thr | Gly | Gly | Val | Val | Ser | Leu | Pro | Asp | Glu | Ala | Asn | Ala | Gln | Ile |
|  | 50 |  |  |  |  | 55 |  |  |  |  | 60 |  |  |

| Gln | Glu | Arg | Leu | Arg | Pro | Tyr | Asn | Ile | Ile | Asn | Asp | Asp | Ser | Ser | His |
| 65 |  |  |  |  | 70 |  |  |  |  | 75 |  |  |  |  | 80 |

| Phe | Asp | Arg | Lys | Lys | Arg | Phe | Pro | Asn | Asn |
|  |  |  |  | 85 |  |  |  |  | 90 |

( 2 ) INFORMATION FOR SEQ ID NO:25:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:25:

GACTCGAGTC GACATCGATT TTTTTTTTT TTTTTTT     37

( 2 ) INFORMATION FOR SEQ ID NO:26:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:26:

CGCTCTAGAG ACTCGAGTCG ACATCGA     27

COMPOUNDS COMPRISING GONADOTROPIN RELEASING HORMONE (GNRH) AND METHODS FOR CONTROLLING REPRODUCTION IN FISH

1. INTRODUCTION

The present invention relates to novel peptide hormones which influence the release of gonadotropins by the pituitary gland in fish. In addition, the present invention is directed to methods of administering such novel peptides to fish so as to control their reproduction. Furthermore, the present invention relates to isolated cDNA encoding the precursor of the novel form of gonadotropin-releasing hormone, and the use of such cDNA in controlling the gonadal development and spawning of fish.

2. BACKGROUND OF THE INVENTION

Marine aquaculture in general, and fish farming in particular, have been extensively developed in recent years. While there has been considerable success in achieving high yields in rearing fish, there has been only limited success in the manipulation of the reproductive cycles and spawning of the reared fish. Such manipulation is a prerequisite for the further development of fish farming into a major agricultural industry.

Many of the economically important fish do not reproduce spontaneously in captivity. This is the case with mullet (*Mugil cephalus*), rabbitfish (*Siganus sp.*), milkfish (*Chanos chanos*), striped bass (*Motone saxatilis*), sea bass (*Dicentrarchus labtax*), seabream (*Sparus aurata*), catfish (*Clarias sp.*) and others. In all these species the reproductive failure is located in the female: whereas vitellogenesis is completed, the stages that follow, namely oocyte maturation and ovulation, do not occur, and thus there is no spawning. Instead, vitellogenic follicles undergo rapid atresia.

In some fish species which do ovulate spontaneously in captivity, such as trout and salmon, both Atlantic and Pacific, e.g. Atlantic salmon (*Salmo salar*) and Pacific salmon (*Onchorhynchus sp.*), ovulation is not synchronized and thus egg collection is a very laborious task. Additionally, the subsequent hatching of the fingerlings is not synchronized and therefore the ability to create schools of fingerlings being all at about the same growing stage, which is necessary for economically feasible fish farming, becomes very difficult.

In fish indigenous to temperate zones, such as seabream, seabass, striped bass, cyprinids and salmoneds, reproduction is seasonal, i.e. ovulation and subsequent spawning occur once or several times during a limited season. Inducing such fish to ovulate and spawn out of the natural spawning season might largely contribute to the management of fish farming. For one, out of season egg production may enable full utilization of the fish farm throughout the whole year, by making it possible to have at any given time fish of all ages. Overcoming the restrictions of seasonal spawning, therefore, may enable the marketing of adult fish year round.

Ovulation and spawning in female fish are controlled by pituitary hormones, mainly the gonadotropins (GtH). However, the release of GtH is not spontaneous but rather induced by a gonadotropin releasing hormone (GnRH) which is secreted by the hypothalamus. It has been found in female *Sparus aurata*, that the level of GtH in the pituitary gland increases as the fish approaches its natural spawning season, i.e. winter time. However, this accumulated GtH is not released into the blood, the consequence being that oocytes undergo rapid atresia. In cases where ovulation and spawning do occur, these are always accompanied by a GtH surge in the blood (Stacey et al., 1979, *Gen. Comp. Endocrinol.* 27:246–249; Zohar et al., 1986, *Gen. Comp. Endocrinol.* 64:189–198; Zohar et al., 1987, In: Proceedings of the 3rd Int. Symp. on Reprod. Physiol. of Fish. St. John's, Newfoundland, Canada, August 1987). Such a surge of GtH and the subsequent ovulation and spawning may be induced by injection of GnRH or analogs thereof. The use of natural fish GnRH in inducing ovulation and spawning has been described in U.S. Pat. No. 4,443,368 and the use of various analogs thereof has been described in U.K. Published Patent Application No. 2152342 and in U.S. Pat. No. 4,410,514. The use of luteinizing hormone releasing hormones (LHRH) for inducing spawning in fish has been described in Japanese Published Patent Application 80-40210.

The administration of GnRH and the genetic manipulation of its production are therefore excellent candidates for methods of manipulating ovulation and spawning in fish. Methods of administering GnRH and its analogs to fish are described in detail in U.S. Pat. No. 5,288,705 (particularly describing implantation and sustained release), which is incorporated herein by reference in its entirety, and in U.S. Pat. No. 5,076,208 (particularly describing ultrasound mediated uptake in an aquatic medium), which is also incorporated herein by reference in its entirety.

GnRH is a ten amino-acid peptide, synthesized in the hypothalamus and released into the hypophysial portal blood system or directly into the pituitary gland in the case of teleost fish. In the pituitary, GnRH regulates GtH secretion by the gonadotroph cells. Gonadotropins, in turn, stimulate steroidogenesis in the gonads and thereby control oogenesis and spermatogenesis.

Previously, eight forms of GnRH had been isolated from vertebrate brains and characterized. (FIG. 1). They are traditionally named for the species from which they were first isolated. The eight previously known members of the GnRH peptide family are all decapeptides with a highly conserved structure: modified N-terminal (pGlu) and C-terminal ($NH_2$) residues, and, with the exception of jawless fish GnRHs, conserved amino acids at position 1–4, 6, 9 and 10. For the remaining positions, amino acid 7 is either Trp or Leu and amino acid 5 is either His or Tyr, whereas amino acid 8 was found to be highly variable.

The first GnRH was isolated and characterized from mammals in the early 1970s (Matsuo et al., 1971, *Biochem. Biophys. Res. Commun.* 43:1334–1339; Schally et al., 1971, *Biochem. Biophys. Res. Commun.* 43:393–399; Amoss et al., 1971, *Biochem. Biophys. Res. Commun.* 44:205–210) and is now referred to as mammalian GnRH (mGnRH). mGnRH is the main GnRH form present in mammals and has also been reported to be present in amphibia and a number of primitive bony fishes (Conlon et al., 1993, *Endocrinology* 132:2117–2123; King et al., 1990, *Peptides* 11:507–514; and Sherwood et al., 1991, *Gen. Comp. Endocrinol.* 84:44–57). Two GnRH forms have been isolated from chicken hypothalamus; chicken GnRH-I (cGnRH-I) (King et al., 1982, *J. Biol. Chem.* 257:10729–10732) and chicken GnRH-II (cGnRH-II) (Miyamoto et al., 1984, *Proc. Natl. Acad. Sci. U.S.A.* 81:3874–3878). cGnRH-II apparently is present in all jawed vertebrates except for placental mammals. Another important GnRH variant has been isolated from salmon (sGnRH) (Sherwood et al., 1983, *Proc. Natl. Acad. Sci. U.S.A.* 80:2794–2798) and was subsequently found to be widely distributed amongst the teleost species. Other species-specific GnRH variants have been and sequenced in catfish (cfGnRH) (Ngamvonchon, et al., 1992, *Mol. Cell. Neurosci.* 3:17–22) and dogfish (dfGnRH) (Lovejoy et al., 1992, *Proc. Natl. Acad. Sci. U.S.A.* 89:6373–6377) and two forms in lamprey; lamprey GnRH-I (Sherwood et al., 1986, *J. Biol. Chem.* 261:4812–4819) and lamprey GnRH-III (Sower et al., 1993, *Endocrinol.* 132:1125–1131).

The cDNA sequences encoding mGnRH, cGnRH-I, cfGnRH, sGnRH and cGnRH-II precursors have been isolated and characterized from mammals and amphibia, birds and teleost fish (see references in Table 1, and FIG. 9). These cDNAs predict a precursor polypeptide consisting of a leader peptide at the N-terminal in direct linkage with the GnRH decapeptide; followed by a 3 amino acid processing site (Gly-Lys-Arg); and an additional peptide called GnRH associated peptide (GAP). The precursor is processed by cleavage at the dibasic amino acids (Lys-Arg). GnRH and GAP are then stored within the secretory granules until secreted (Wetsel et al., 1991, *Endocrinol.* 129:1584–1594).

isolated cDNA encoding the sbGnRH precursor, comprising the coding regions for the sbGnRH signal peptide, the sbGnRH decapeptide, the conserved cleavage site, and an associated peptide called GnRH associated peptide (GAP). The present invention additionally provides methods for manipulation of ovulation and spawning in fish using the sbGnRH peptide and analogs thereof and the cDNA encoding sbGnRH.

4. DESCRIPTION OF THE FIGURES

FIG. 1. Amino acid sequences of known GnRH forms. The structure of the eight previously known GnRH forms (SEQ ID NOS: 11 –18) and sbGnRH (SEQ ID NO: 3) are shown along with the conventionally accepted nomenclature (GnRH peptides are usually named for the species from which they were first isolated). The different forms are listed in order of similarity to sbGnRH. Regions that demonstrate differences are highlighted within a box.

TABLE 1

Characterized cDNAs of GnRH precursors.

| GnRH form | Species | References |
|---|---|---|
| mGnRH | Human | Seeburg & Adelman 1984 Nature 311:666–668. |
| | Rat | Adelman et al. 1986 Proc. Natl. Acad. Sci. USA 83: 179–183. |
| | Mouse | Mason et al. 1986 Science 234: 1372–1378. |
| | Frog | Hayes et al. 1994 Endocrinology 134(4): 1835–1845. |
| cGnRH-I | Chicken | Dunn et al. 1993 J. Mol. Endocrinol. 11: 19–29. |
| CfGnRH | Catfish | Bogerd et al. 1994 Eur. J. Biochem. 222(2): 541–549. |
| sGnRH | African cichlid | Bond et al. 1991 Mol. Endocrinol. 5: 931–932. |
| | Rainbow trout | Alestrom et al. 1992 Mol. Marine Biol. and Biotech. 1(4+5): 376–379. |
| | Atlantic salmon | Klungland et al. 1992 Mol. and Cell. Endocrin. 84: 167–174. |
| | Masu salmon | Suzuki et al. 1992 J. Mol. Endocrin. 9: 73–82. |
| | Sockeye salmon | Ashihara et al. 1994 Sequence listing copied from a poster which appeared at the IUBS Symposium on "Advances in the Molecular Endocrinology of Fish," May 23–25, 1993, Toronto, Canada. |
| cGnRH-II | catfish | Bogerd et al. 1994 Proc. Natl. Acad. Sci. USA 91: 1423–1427. |
| | African cichlid | White et al. 1994 |

Despited the knowledge of these other GnRH's, there remains a need in marine aquaculture for more effective manipulation of reproduction. Obtaining the most physiologically relevant form of the GnRH hormone and its gene will greatly contribute to improving the efficiency of controlling fish reproduction.

The following abbreviations are used in this application in addition to the usual abbreviations for the trivial names of the more common α-amino acids:

Nva=norvaline
Orn=ornithine
Ile=isoleucine
Nle=norleucine
Nal=β-naphthyl-Ala
Phg=C-phenylglycine
Abu=2-aminobutyric acid
Chg=2-cyclohexyl Gly
OMe=methylester
OBzl=benzyl ester
tBu=tertiary butyl
BOC=tert-butyloxycarbonyl

3. SUMMARY OF THE INVENTION

The present invention provides a previously unknown purified peptide and analogs thereof which exhibit gonadotropin-releasing activity. This peptide, a gonadotropin releasing hormone (GnRH), was isolated from the gilthead seabream, *Sparus aurata*, and has been named sbGnRH. Not only is the peptide of the present invention novel, the information provided herein indicates it is more physiologically important in fish than previously characterized GnRH's. Furthermore, the present invention provides FIG. 2. Purification of GnRH from seabream brains. Percent of acetonitrile is shown by a solid line. Panel A. irGnRH was eluted from Sep-Pak HPLC using TFA in the mobile phase from lot B brains. Panel B. irGnRH from lot B brains was eluted from a $C_{18}$ column using HFBA in the mobile phase. Panel C. Purification of SB-II and SB-III using a $C_{18}$ column with the isocratic TEAF HPLC method. Samples were from late-eluting fractions in all lots of brains after step 1 (Table 2).

Figure 3:
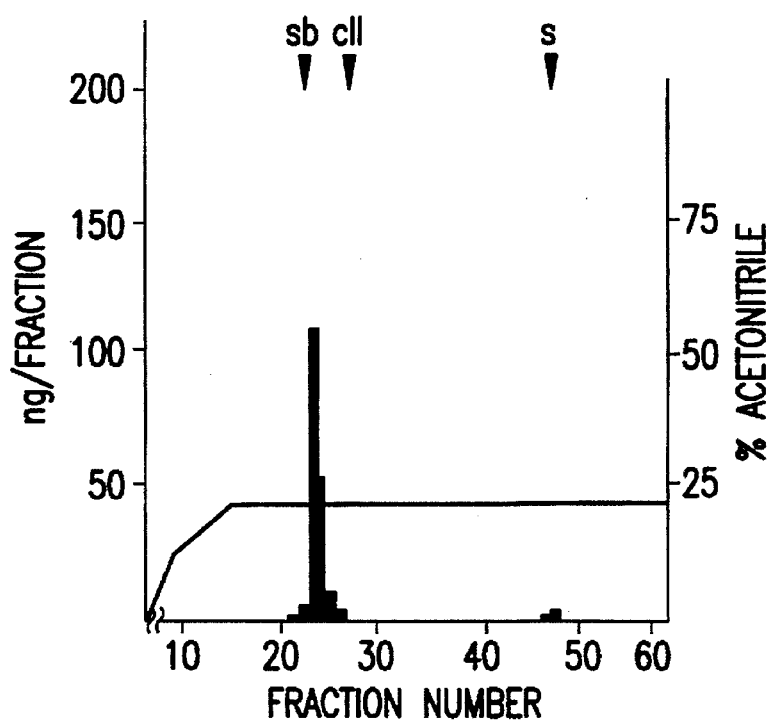

FIG. 3. HPLC analysis of GnRH from seabream pituitaries. Percent acetonitrile is shown by solid line. irGnRH was eluted from a $C_{18}$ column using an isocratic method using TEAF and acetonitrile as mobile phase. The elution positions of synthetic standards are indicated by arrows (sb= sbGnRH, cII=cGnRH-II, s=sGnRH).

Figure 4:
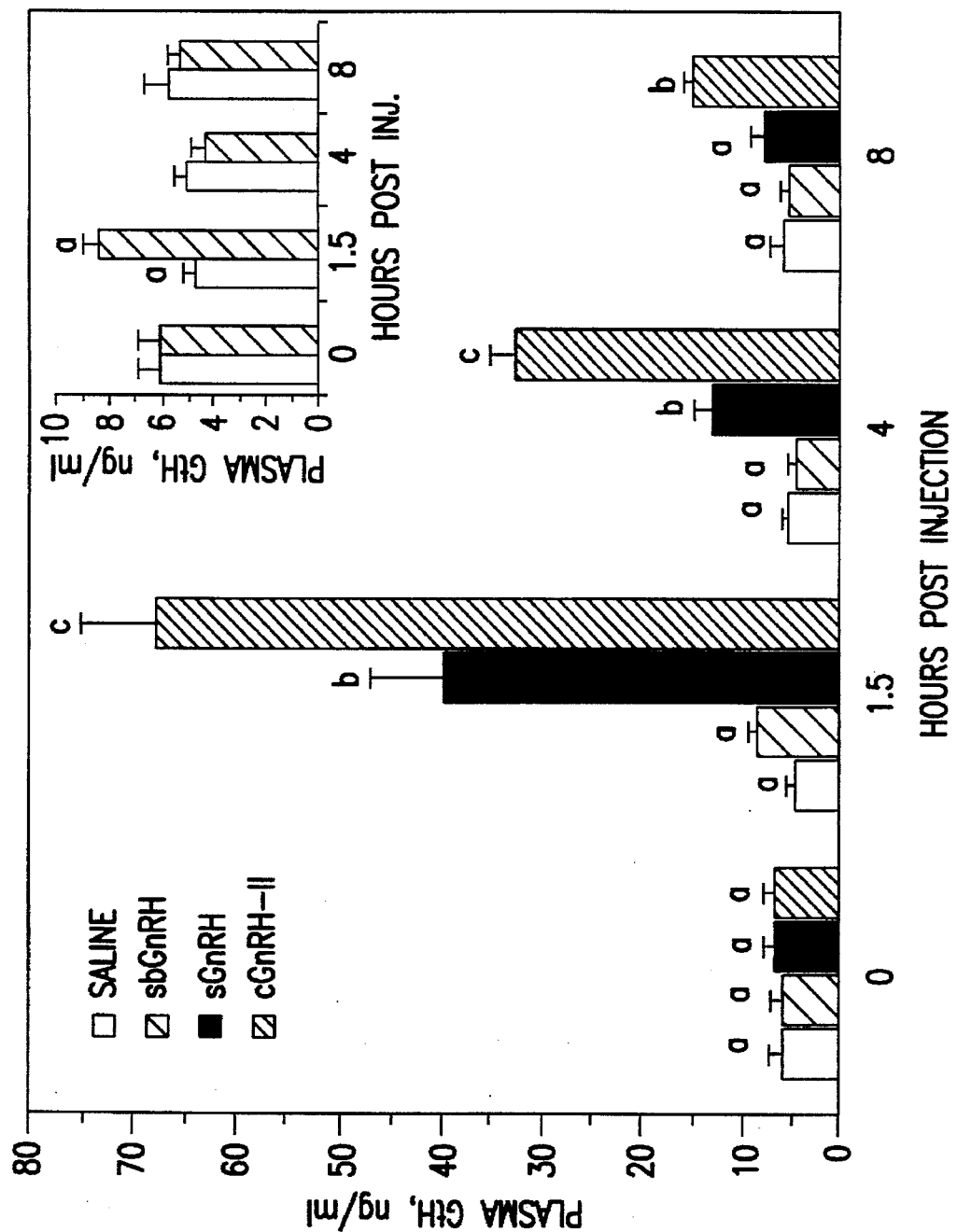

FIG. 4. Plasma levels of GtH-II (means±SEM, n=8) in female gilthead seabream before injection, and at 1.5, 4 and 8 hours after the injection of 5 µg/kg body weight of the three native forms of GnRH present in seabream brain. Inset shows GtH-II levels in response to saline and sbGnRH. For each sampling time, bars marked by different letters are significantly different (P<0.01). sb, seabream; s, salmon; c, chicken; GnRH, gonadotropin-releasing hormone; GtH, gonadotropin-II.

Figure 5:
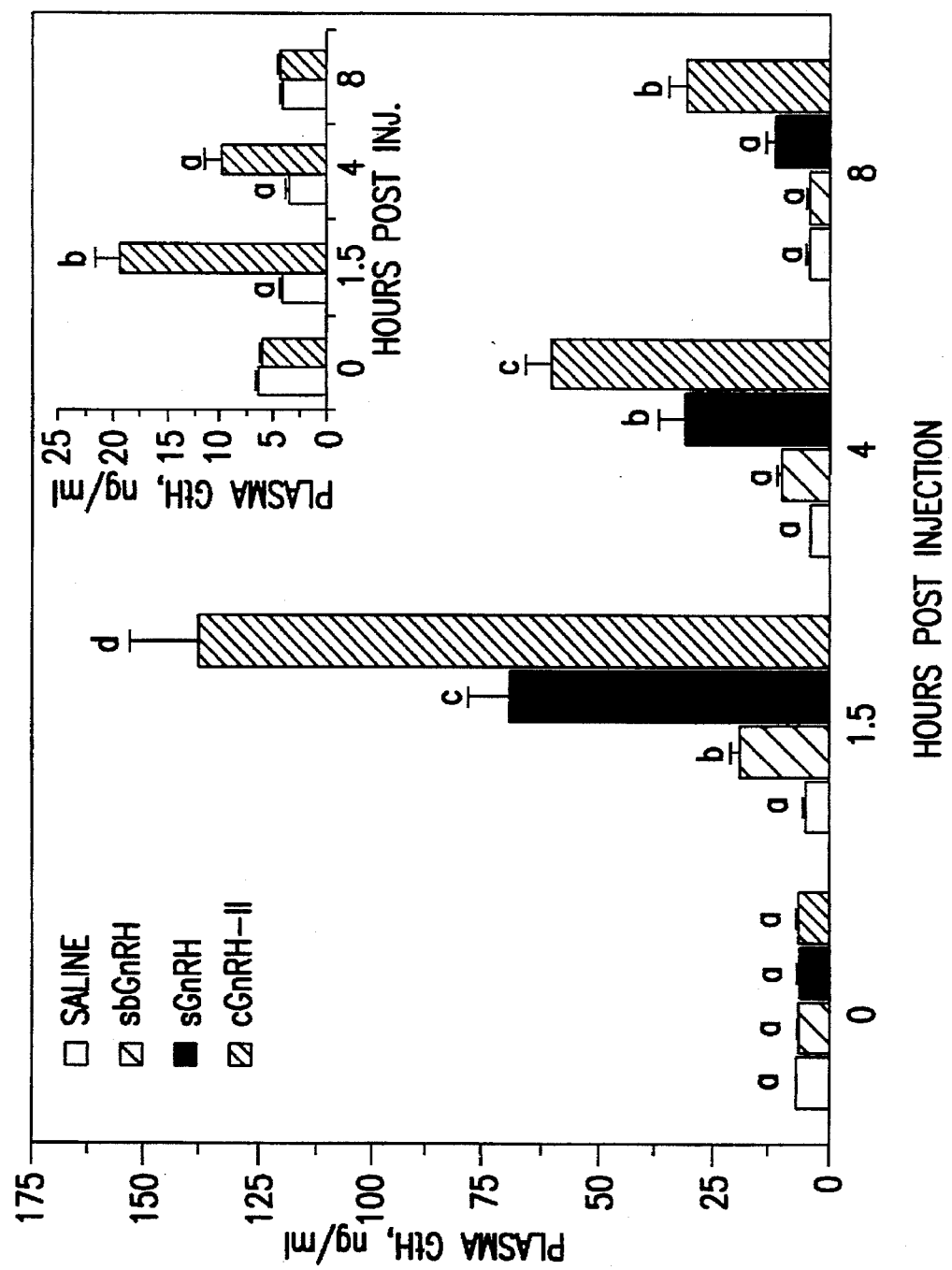

FIG. 5. Plasma levels of GtH-II (means±SEM, n=8) in female gilthead seabream before injection, and at 1.5, 4 and 8 hours after the injection of 25 µg/kg body weight of the three native forms of GnRH present in seabream brain. Inset shows GtH-II levels in response to saline and sbGnRH. For each sampling time, bars marked by different letters are significantly different (P<0.05). sb, seabream; s, salmon; c, chicken; GnRH, gonadotropin-releasing hormone; GtH, gonadotropin-II.

Figure 6:
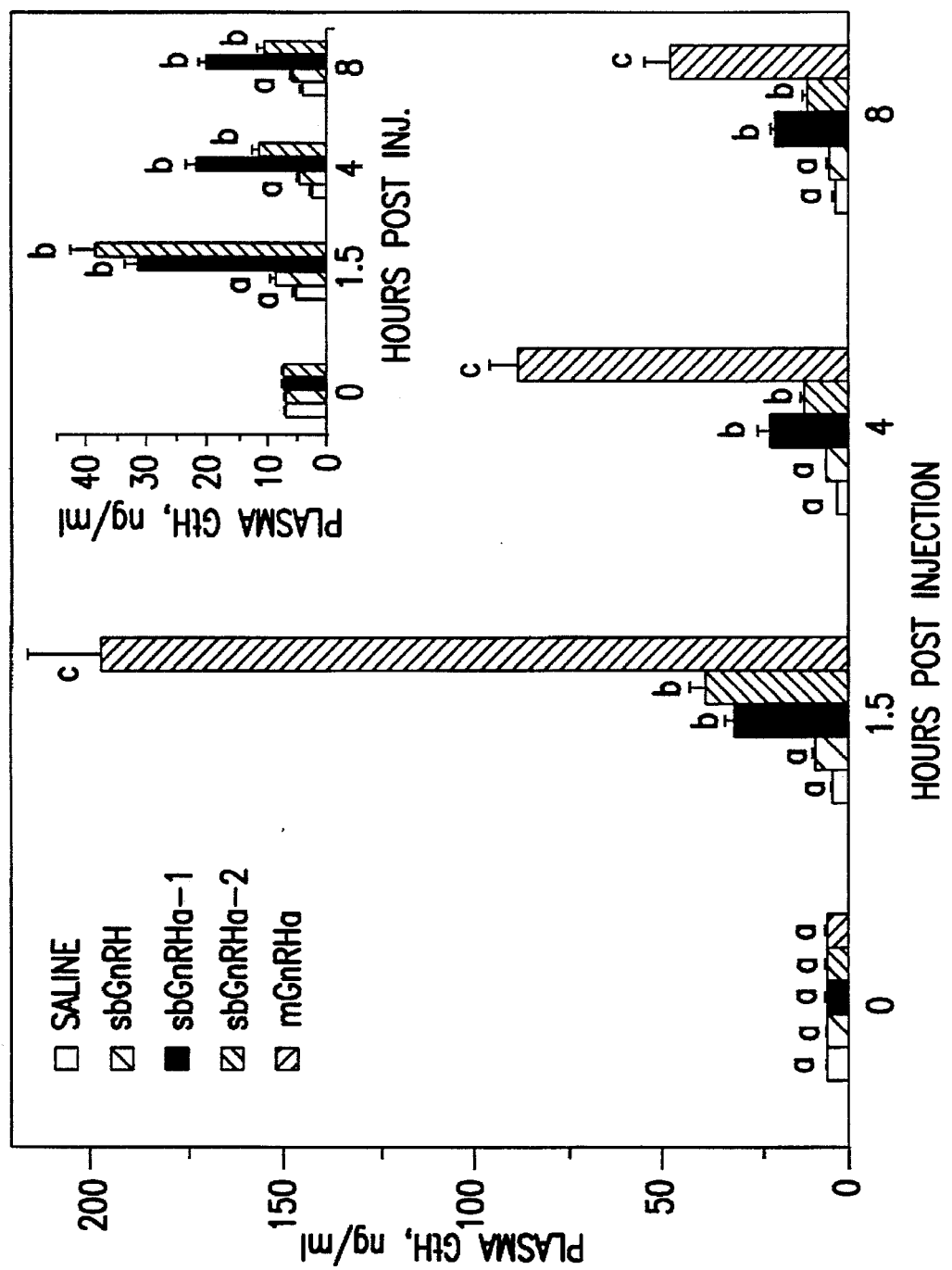

FIG. 6. Plasma levels of GtH-II (means±SEM, n=8) in female gilthead seabream before and at 1.5, 4 and 8 hours after the injection of 5 μg/kg body weight of native sbGnRH, two of its analogs (also shown in inset) and an analog of mammalian GnRH. sbGnRHa-1=[D-Ala$^6$, Pro$^9$-NEt]-sbGnRH; sbGnRHa-2=[D-Arg$^6$, Pro$^9$-NEt]-sbGnRH; mGnRHa =[D-Ala$^6$, Pro$^9$-NEt]-mGnRH. For each sampling time, bars marked by different letters are significantly different (P<0.01). sb, seabream; m, mammalian; GnRHa, gonadotropin-releasing hormone analog; GtH, gonadotropin-II.

FIG. 7. Degenerate oligonucleotides for PCR amplification of sbGnRH precursor. The amino acid sequence for pre-sbGnRH (SEQ ID NO: 4) is based on the assumption that sbGnRH is processed similarly to other forms of GnRH. Two pools of degenerate 5' primers were designed according to amino acids 1–8 and used in two different PCR reactions (SEQ ID NOS: 5 and 6). The two nucleotides which differ in these two primers are underlined. Only the portions of the degenerate primers' sequences that overlap the pre-sbGnRH peptide sequence are shown. The full-length sequences of the degenerate primers are provided in Section 8.1.1, below. An internal sequence was chosen for use as a probe and was designed according to amino acids 8–13 (SEQ ID NO: 7). It was used to identify a single band corresponding to the sbGnRH precursor in the smear of amplified PCR products.

FIG. 8. The cDNA encoding for the seabream GnRH precursor (SEQ ID NO: 1). The nucleotide sequence shown was obtained from sequencing both strands of the four clones isolated from the library which ultimately proved to be identical four. The deduced amino acids are displayed using the one letter code and are numbered relative to Q—the first amino acid of the GnRH decapeptide (underlined). *=stop codon. Polyadenylation signal is underlined.

FIG. 9. Alignment of GnRH-precursor peptide sequences (SEQ ID NOS: 2, 19–24). The functional domains of the deduced peptide are indicated above the sequence. The GnRH decapeptide sequence is indicated by the darker shade box. Boxed regions indicate similarity between amino acids found in different GnRH precursors.

Figure 10:
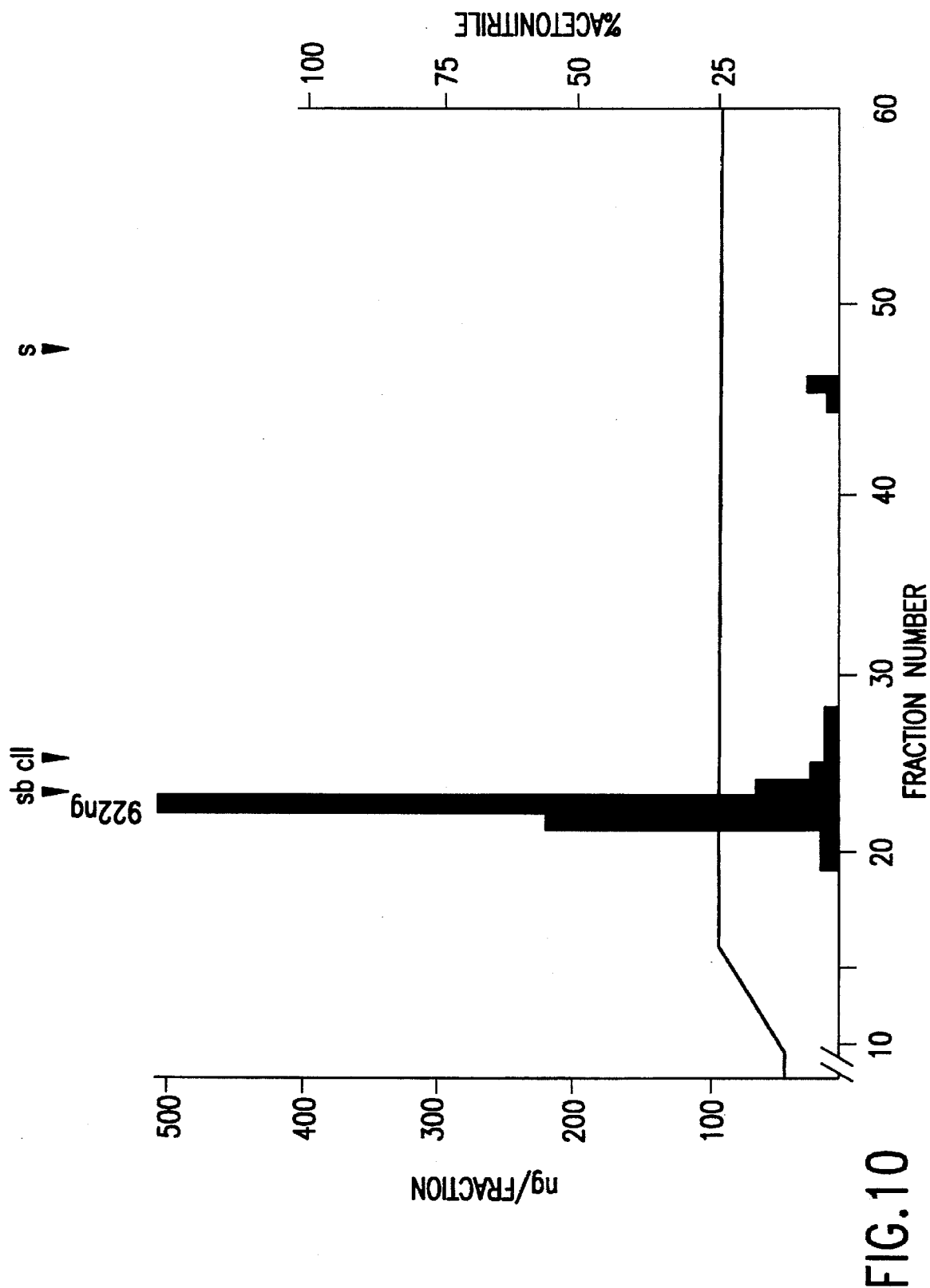

FIG. 10. HPLC analysis is GnRH from striped bass pituitaries. Percent acetonitrile is shown by solid line. irGnRH was eluted from a $C_{18}$ column using an isocratic method using TEAF and acetonitrile as mobile phase. The elution positions of synthetic standards are indicated by arrows (sb=sbGnRH, cII=cGnRH-II, s=sGnRH).

5. DETAILED DESCRIPTION OF THE INVENTION

The present invention relates to a novel form of GnRH. The invention is based, in part, on the applicants' discovery of three distinct forms of GnRH isolated from the brain of gilthead seabream, Sparus aurata. One of these forms has a novel structure and is called sbGnRH. The other two are previously known forms, cGnRH-II and sGnRH. While the occurrence of two forms of GnRH in a single species has been commonly reported, there are no known reports of three forms having been directly identified in one species. sbGnRH is active in causing the release of gonadotropin hormone-II (GtH-II) from the pituitary gland, although it is less active than cGnRH-II and sGnRH. The dominant form of GnRH stored in the pituitary, however, is sbGnRH. Not only is the content of sbGnRH 500 fold greater than that of sGnRH, but cGnRH-II was not detected in the pituitary. Such evidence strongly indicates that sbGnRH is the endogenous releaser of GtH-II in seabream. Furthermore, similar evidence of this novel peptide's overwhelming abundance in the pituitaries of hybrid stiped bass support this conclusion and strongly suggest a physiologically important role in a wide range of finfish. sbGnRH may also be effective in the control of reproduction of invertebrate fish such as bivalves, molluscs, and crustaceans.

The sbGnRH peptide has a similar amidated decapeptide structure to other GnRH's, but has a unique serine residue at position 8 (FIG. 1). Analogs of sbGnRH that include substitutions at position 6, and at position 9–10 possess higher GtH-II-releasing activity than the endogenous peptide.

The sbGnRH peptide and analogs thereof, hereinafter referred to as active compound, of the present invention may be administered to the fish to induce gonadal development and to induce and synchronize ovulation, spawning, sperm production, and spermiation. Any of a number of methods of administration which are routinely practiced in the art may be used, as described in this section, below.

The active compound may consist of the endogenous sbGnRH peptide, as described in FIG. 1, or an analog of such a peptide, or any combination of such endogenous and/or analog peptides.

Native GnRH is susceptible to rapid degradation in the blood due to cleavage of the decapeptide, particularly at positions 5–6 and 9–10. Analogs having different amino acids at the relevant positions which renders them less sensitive to such enzymatic degradation are thus preferred for use in the compositions according to the present invention. Such analogs may be selected from a group including but not limited to, [D-Ala$^6$,Pro$^9$-NEt]-sbGnRH and [D-Arg$^6$,Pro$^9$-NEt]-sbGnRH, which are described in detail in the example in Section 7, below.

Additional active agents may include, for example, substitutions of positions 6 and/or 7 of the endogenous residues with hydrophobic residues such as D-Trp, for position 6, and L-Trp for position 7. Such substituting amino acids and amino acid derivatives may occur singly or in combination with one another. A list of suitable substitute amino acids and amino acid derivatives contemplated by the invention is presented in U.S. Pat. No. 4,410,514, which is incorporated herein by reference in its entirety. The invention further contemplates peptides with conservative substitutions of Ser at position 8 with such amino acids as Ala, Thr, Pro, and Gly.

The endogenous sbGnRH peptide may be isolated from seabream brains using standard techniques as described in detail in the example below. Preferably, such peptides and peptide analogs, which, for example, constitute the active compound, may be chemically synthesized using standard automated laboratory techniques, as described in detail in the example in Section 7.1.1, below.

In accordance with the invention, a variety of methods well known in the art may be used to administer the sbGnRH peptide and analogs thereof. For example, and not by way of limitation, the active ingredient may be directly injected intramuscularly into the fish. In preferred embodiments, the active compound may be combined with a polymer based carrier matrix into a sustained release delivery system.

The term "sustained release" is understood to mean a gradual release of the active compound in a controlled manner. A suitable carrier having such sustained release properties may be chosen on the basis of its gradual release properties in a solution designed to resemble a fish's plasma, such as a ringer solution, other physiological saline solutions, fish serum, etc.

The polymer based carrier matrix may comprise natural or synthetic polymers or copolymers. Examples of natural polymers are polysaccharides and various proteins. Synthetic polymers or copolymers may either be biodegradable, in which case the sustained release is due to biodegradation, or non degradable, in which case the sustained release is due to gradual diffusion of the active compound therefrom. Examples of biodegradable polymers and copolymers are polylactic polyglycolic acid, polyanhydrides, polyorthoesters and polycaprolactone. Examples of non biodegradable polymers are silicone rubber in a mixture with a relatively large amount of a biocompatible protein, a copolymer of ethylene and vinyl acetate, the relative amount of vinyl acetate being about 20–50%, and various synthetic polysaccharides. In general, any biocompatible polymeric controlled release carrier such as those hitherto used in the art for delivering sbGnRH and analogs thereof, may in principle be used in accordance with the present invention.

The compositions of the present invention are solid and may be prepared in any suitable form such as pellets, discs, rods or microspheres. These may be administered to the fish either by implantation of a composition unit (in the form of a pellet, disc or rod) or by injection, either intramuscular, subcutaneous or intraperitoneal (in the form of a suspension of mini-rods or micro-spheres).

The size of an implantable composition in accordance with the present invention will be determined both by the size of the fish in which implantation thereof is intended, i.e. it should not be too big, and by practical limitations, i.e. the implantable composition should not be too small so as to render it difficult for manipulation. Thus, for example, a disc having a diameter of about 2–10 mm and a thickness of about 1–2 mm has been found to be suitable for implantation in many fish such as the sea bream, sea bass and trout. Similarly, rods being 3–7 mm long and having a cross-sectional area of about 1 mm were also found to be suitable for implantation.

Injectable compositions in accordance with the invention in the form of mini-rods or microspheres should be sufficiently small to pass through a syringe. Injectable compositions will be suspended in an injectable solution, such as saline or various buffers, prior to injection.

Implantable compositions may preferably comprise about 300 μg of the active compounds per unit. When administering an injectable composition in accordance with the invention, the administered composition will preferably comprise about 5–200 μg of the active compound per kg of body weight of the injected fish. The amount of the active compound may, in some cases, be reduced if a very active analog is utilized.

It is known in the art that the release of GtH in fish is regulated both by stimulatory GnRH and also by an inhibitory factor which is most probably dopamine (termed also gonadotropin-release inhibitory factor, GRIF, Peter et al., 1984, *Gen. Comp. Endocrinol.* 55:337–346; Lin et al., 1986, *Gen. Comp. Endocrinol.* 64:389–395). In some fish species, such as cyprinids (Peter et al., 1987, In PROCEEDINGS OF THE FISH BREEDING WORKSHOP, Singapore, Apr. 7–10, 1987. *Aquaculture* 74:1–10), the dopaminergic inhibitory effect on gonadotropin-release is dominant and hence in such cases the compositions in accordance with the present invention should also contain dopaine antagonists such as pimozide or domperidone.

Where it is desired to induce or synchronize the ovulation and spawning within the natural spawning season, only the females will be so treated, since the males are usually ready to spermiate throughout this season. Where, however, it is desired to induce early ovulation and spawning, i.e. outside the natural spawning season, the males will be treated as well. For such a treatment, the fish are slightly anesthetized and a composition in accordance with the present invention is then applied.

The composition may be administered to the fish either by subcutaneous or intra-peritoneal implantation (for injectable micro-rods or spheres). For subcutaneous implantation a small incision are made through the fish's skin at a suitable place and after separating the skin from the underlying muscles, e.g., by the use of forceps, the implantation and incision is made through the skin and muscle of the peritoneal cavity and the implant is inserted through the incision and placed in the peritoneum. The incision in each case is made as small as practicably possible and there is usually no need for post implantational stitching.

For injection, the micro-rods or micro-spheres are suspended in a vehicle solution and thereafter the suspension is injected into a suitable muscle of the fish or into the peritoneal cavity.

After administering the composition, female fish are kept together with one or more spermiating males in containers until the spawned and fertilized eggs may be collected, which eggs are then kept in appropriate containers until batching. The eggs so obtained also constitute an aspect of the present invention.

If all fish in a school intended for reproduction are treated by the method of the invention at about the same time, the resulting ovulation and spawning will be essentially synchronous, and thus collecting of the eggs is much easier and more economical than collecting the eggs in fish induced to spawn as previously performed in the art. Additionally, it will subsequently become much easier to form schools of fingerlings being all about the same age. Furthermore, in many fish species it will be possible to obtain such schools throughout the whole year.

The cDNA of the sbGnRH gene was isolated from seabream brain and sequenced (FIG. 7). The isolated cDNA of sbGnRH reveals a coding region that comprises the coding regions for the sbGnRH signal peptide, the sbGnRH decapeptide, the conserved cleavage site, and an associated peptide called GnRH associated peptide (GAP) (FIG. 9). Such a cDNA may be isolated by standard laboratory techniques such as those described in detail in the example in Section 8.1, below.

The DNA molecules of the present invention, may be used to induce or inhibit gonadal development, and to induce and synchronize ovulation, spawning, sperm production, and spermiation. In order to induce such sexually reproductive activities, the precursor cDNA, or a portion thereof (e.g. encoding the sbGnRH decapeptide and/or GAP) may be transfected into fish. Tranfection may be achieved, for example and not by way of limitation, by microinjection, retroviral-mediated integration, electoporation, liposome—mediated delivery, and by high velocity microprojectiles. For a review of such transgenic systems in fish, see Chen, et al., 1990, *Tibtech* 8:209–215 which is incorporated herein by reference in its entirety.

Such a transfected coding sequence may be operatively linked to an inducible promoter using standard laboratory techniques routinely practiced in the art, such that expression may be controlled experimentally. See, for example, Ausubel F. M. et al., eds., 1989, *Current Protocols in Molecular Biology,* Vol. I, Green Publishing Associates, Inc., and John Wiley & sons, Inc., New York; and Sambrook et al., 1989, *Molecular Cloning: A Laboratory Manual,* Cold Spring Harbor Laboratories Press, Cold Spring Harbor, N.Y., which are incorporated herein by reference in their entireties. Controlled induction may therefore result in an increase in expression at the appropriate stage of development. Such controlled induction of expression is particularly useful in the production of brute stock for fish breeding.

Conversely, the DNA sequences of the present invention may be used to inhibit gonadal development. For example, once fish are bred, a grow out stock is raised for harvest. In order to maximize the overall growth of this stock for harvest and ultimate consumption, it is advantageous to inhibit the gonadal development. In addition, the inhibition of gonadal development may be used in order to produce sterile fish. Such sterile fish are important in transplanting exotic species into environments where their propagation is undesirable.

Such inhibition of gonadal development may be achieved by the negative regulation of GnRH. Among the compounds which may exhibit the ability to regulate negatively GnRH are antisense, ribozyme, and triple helix molecules. Such molecules may be designed to reduce or inhibit either wild type, or if appropriate, mutant target gene activity. Techniques for the production and use of such molecules are well known to those of skill in the art.

Anti-sense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the target gene nucleotide sequence of interest, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridize with complementary oligonucleotides, using ribonuclease protection assays.

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

It is possible that the antisense, ribozyme, and/or triple helix molecules described herein may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. To ensure that substantially normal levels of target gene activity are maintained, therefore, nucleic acid molecules that encode and express target gene polypeptides exhibiting normal target gene activity may, for example, be introduced into cells via gene therapy methods such as those described, below, in this section that do not contain sequences susceptible to whatever antisense, ribozyme, or triple helix treatments are being utilized. Alternatively, it may be preferable to coadminister normal target gene protein into the cell or tissue of interest in order to maintain the requisite level of cellular or tissue target gene activity.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

The invention contemplates, in addition to the DNA sequences disclosed herein, 1) any DNA sequence that encodes the same amino acid sequence as encoded by the DNA sequences shown in FIG. 8; 2) any DNA sequence that hybridizes to the complement of the coding sequences disclosed herein (see FIG. 8) under highly stringent conditions, e.g., washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and/or 3) any DNA sequence that hybridizes to the complement of the coding sequences disclosed herein (see FIG. 8) under less stringent conditions, such as moderately stringent conditions, e.g., washing in 0.2×SSC/0.1% SDS at 42° C. (Ausubel et al., 1989, supra), yet which still encodes a functionally equivalent gene product.

The invention also encompasses 1) DNA vectors that contain any of the coding sequences disclosed herein (see FIG. 8), and/or their complements (i.e., antisense); 2) DNA expression vectors that contain any of the coding sequences disclosed herein (see FIG. 8), and/or their complements (i.e., antisense), operatively associated with a regulatory element that directs the expression of the coding and/or antisense sequences; and 3) genetically engineered host cells that contain any of the coding sequences disclosed herein (see FIG. 8), and/or their complements (i.e., antisense), operatively associated with a regulatory element that directs the expression of the coding and/or antisense sequences in the host cell. Regulatory element includes, but is not limited to, inducible and non-inducible promoters, enhancers, operators and other elements known to those skilled in the art that drive and regulate expression. The invention includes fragments of any of the DNA sequences discussed or disclosed herein.

6. EXAMPLE: PURIFICATION AND IDENTIFICATION OF GnRH IN SEABREAM 6.1. MATERIALS AND METHODS 6.1.1. Collection of Brains and Extraction of Peptides A total of 1.8 kg of intact brains (10,000) and dissected hypothalami (2,500) were collected from mature male and female gilthead sea bream during the spawning season (January). The tissues were immediately frozen in liquid nitrogen and stored at −90.5° C. Brains were divided into four groups; lots A, B, and C were predominantly brains and some hypothalami, whereas lot D was predominantly hypothalami.

For each lot, the brain tissue was cooled with liquid nitrogen and powdered in a Waring blender. Extraction of peptides with acetone and HCl and subsequent removal of substances soluble in petroleum ether were done as previously described (Lovejoy, et al., 1992, *Proc. Natl. Acad. Sci. U.S.A.* 89:6373–6377). The final aqueous phase for each lot was evaporated in a vacuum centrifuge to a volume less than 500 ml. Each extract was pumped onto separate columns of 10 Sep-Pak (Millipore, Millford, Mass.) cartridges in series.

Each Sep-Pak column was connected to a Beckman model 166 HPLC. Solvent A was 0.05% Trifluoroacetic acid (TFA) in water; solvent B was 80% acetonitrile, 19.95% water and 0.05% TFA. A gradient was applied at an increasing rate of 1.4% solvent B/min and a flow rate of 1 ml/min. Eluant was collected in 1 ml fractions for 60 min. Aliquots of 10 μl from each fraction were used for RIA to determine immunoreactive GnRH (irGnRH, see Section 6.1.3 below for antisera). Fractions that contained irGnRH in each lot were pooled and reduced in volume in a vacuum centrifuge.

6.1.2. HPLC Analysis

Further HPLC steps for purification of sea bream immunoreactive GnRH (irGnRH) are outlined in Table 2. After Sep-Pak HPLC (step 1), each lot of extract was subjected to HPLC using a HFBA gradient program (step 2). Early-eluting irGnRH fractions from all lots were pooled from step 2 and designated sea bream GnRH I (sbGnRH-I) Further purification of sbGnRH-I is outlined as steps 3–5 in Table 2.

Late-eluting irGnRH fractions for all lots from step 2 HPLC runs were combined, reduced in volume and applied to step 3 (Table 3). Step 3 of this procedure had an isocratic portion of the program that separates sGnRH from other irGnRH forms (Sherwood et al., 1993, *Regul. Pept.* 46:523–534). The early- and late-eluting irGnRH fractions from this step were designated sbGnRH-II and sbGnRH-III, respectively. Purification of sbGnRH-II and -III followed steps 4 and 5 in Table 3.

6.1.3. RIA Measurement

Aliquots of 10 μl from fractions collected at each successive step in the purification were assayed for irGnRH by methods previously described (Sherwood, et al., 1983, *Proc. Natl. Acad. Sci. U.S.A.* 80:2794–2798). Heterologous assays were used with mammalian (mGnRH) as the labeled hormone and standards. Antiserum GF-4 was used in a final dilution of 1:5,000 resulting in 26–37% binding of $^{125}$I-mGnRH. Antiserum GF-4 recognizes 6 of the 8 known forms of GnRH (Lovejoy et al., supra; Kelsall et al., 1990, *Gen. Comp. Endocrinol.* 78:479–494; Ngamvonchon, et al., 1992, *Mol. Cell. Neurosci.* 3:17–22). Lamprey GnRH-I is not recognized by GF-4, whereas lamprey GnRH-III has not been tested. Limits of detection (B/B°=80%) averaged 7.2 pg. Serial dilutions were done if fractions of 10 μl had values of irGnRH that exceeded B/B°=20%. Antiserum R-42 does not recognize forms of GnRH that are altered at the N- and C-termini (Kelsall, et al., supra; Copeland, et al., 1979, *Encocrinology* 104:1504–1512). R-42 therefore, was used after the last step in the purification to verify that the peptide was intact. A dilution of 1:100,000 of R-42 had a binding of 31% and a limit of detection of 2.8 pg.

6.1.4. Characterization of the primary structure

An aliquot (10% by volume) of the peptides purified by HPLC on a phenyl column (Step 5, Table 2) was subjected to a narrow-bore $C_{18}$ column employing 0.05% TFA and acetonitrile for elution. Fractions were collected and analyzed with a Bruker Reflex matrix assisted laser desorption/ ionization (MALDI) time-of-flight mass spectrometer. When accurate mass measurements were required, these were carried out with a JEOL HX100 mass spectrometer operating in a liquid secondary ionization (LSI) mode using an accelerated voltage/electric field scan as previously described (Lovejoy et al., supra). The residual 90% of the samples was concentrated to dryness in a Savant Speed Vac concentrator and subjected to pyroglutamate amino peptidase treatment as previously described (Fischer, et al., 1992, *J. Prot. Chem.* 11:336). This was followed by HPLC separation and sequence analysis on an ABI Protein Sequencer (Model 470A) (Applied Biosystems, Inc., Seattle, Wash.).

6.1.5. Peptide Synthesis

Solid phase synthesis of sbGnRH was carried out on a methylbenzhydrylamine resin (Boc strategy) using previously established methods (Rivier, et al., 1992, *J. Med. Chem.* 35:4270–4278) and the following protecting groups: pryo-Glu (carbobenzoxy), Boc-His (tosyl), Boc-Ser (Benzyl) and Boc-Tyr (2-bromo-carbobenzoxy). sbGnRH was deprotected and cleaved from the solid support with hydrofluoric acid. After purification with reverse phase HPLC (>97% pure) in two solvent systems (Rivier et al., 1984, *J. Chromatog.* 228:303 –328), the structure was confirmed by mass spectral and amino acid composition analyses.

6.1.6 HPLC Analysis of Pituitary Extract

Sea bream pituitaries (100, 0.75 g total) were collected during the spawning season from two-year-old females with preovulatory oocytes (500–600 μm external diameter). In a separate experiment hybrid striped bass pituitaries (100, 0.75 g total) were also collected. The pituitaries were extracted for peptides as described above in Section 6.1.1. The extract was applied to a separate $C_{18}$ HPLC column and eluted using an isocratic method (Table 3, step 3). Reference peptides of sbGnRH, cGnRH-II and sGnRH (200 ng each) were applied to the HPLC column after the pituitary extract and the procedure repeated. Fractions (1 ml) were collected separately for each HPLC application and assayed for irGnRH. A blank (800 μl solvent A injected) HPLC was done prior to that of the pituitary extract. irGnRH was not detected in 500 μl of each blank fraction.

6.2. RESULTS 6.2.1 Initial HPLC Analysis

Assay of HPLC fractions from the 4 lots that eluted from the Sep-Pak columns showed irGnRH activity in fractions 21–41 (FIG. 2A). Fractions that contained less than 15 ng/fraction of irGnRH activity were not used in subsequent steps.

6.2.2. sbGnRH-I Purification (Novel sbGnRH)

Figure 2B:
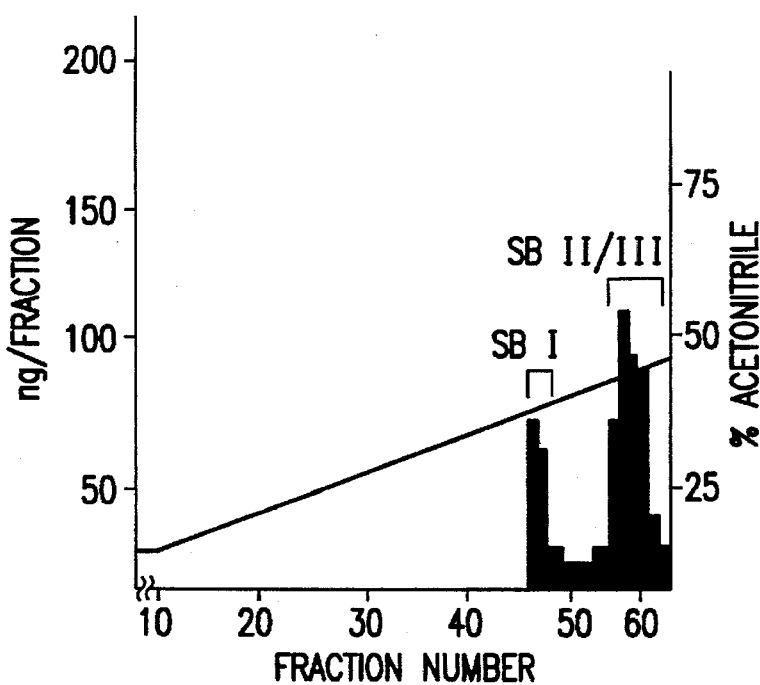

Each HPLC run in step 2 showed an early-eluting peak at 46 min. (FIG. 2B). These irGnRH fractions (initially called sbGnRH-I) from the 4 lots were pooled and shown to contain a total of 153 ng of irGnRH. A large proportion (110 ng) of the combined irGnRH was derived from lot D containing predominantly hypothalamic tissue.

In step 3 of the purification, 297 ng of irGnRH was detected in fractions 33 and 34 with less than 10 ng of activity in the next 4 fractions. Fractions 33 and 34 were combined for step 4 of the procedure. Three fractions (28–30) were found to have a total of 220 ng of irGnRH and were further purified. At the last step of the purification, fractions 23 and 24 contained 232 ng of irGnRH. Fraction 23 (179 ng -irGnRH) was selected for digestion with pyroglutamyl aminopeptidase and protein sequencing. RIA using antiserum R-42 confirmed the presence of intact irGnRH in these fractions, but detected only 82 ng in fraction 23 and 120 ng in combined fractions 23 and 24.

TABLE 2

HPLC steps in the purification of sbGnRH-I (novel sbGnRH) from sea bream brains.

| Step | Solvents: A | Column Type B | | Gradient |
|---|---|---|---|---|
| 1 | 0.05% TFA* | 0.05% TFA in 80% ACN | Sep-Pak $C_{18}$ | 5–80% B in 55 min |
| 2 | 0.1M HFBA | 0.1M HFBA in 75% ACN | $C_{18}$ | 5–65% B in 60 min |
| 3 | 0.13M TEAF | ACN | $C_{18}$ | 5–60% B in 55 min |
| 4 | 0.13M TEAP | ACN | $C_{18}$ | 5–20% B in 10 min 20–40% B in 40 min |
| 5 | 0.05% TFA | 0.05% TFA in 80% ACN | Phenyl | 5–20% B in 10 min, 5–20% B in 40 min |

*Chemical abbreviations:
TFA: trifluoroacetic acid pH 2.0
HFBA: heptafluorobutyric acid pH 2.5
TEAF: triethylamine formate pH 2.5
TEAP: triethylamine phosphate pH 6.5

Edman degradation of the pyroglutamate amino peptidase—treated fraction of sbGnRH-I yielded the sequence:

His-Trp-Ser-Tyr-Gly-Leu-Ser-Pro-Gly (SEQ ID NO: 8).

Based on the novelty of the Ser residue at position eight, this peptide was named, in accordance with the invention, sbGnRH. The molecule ion mass of the non-treated sbGnRH-I fraction was m/z 1113.6 (LSI). The calculated monoisotopic mass ($MH^+$) for pGlu-His-Trp-Ser-Tyr-Gly-Leu-Ser-Pro-Gly-$NH_2$ (SEQ ID NO: 3) (elemental composition $C_{52}H_{69}N_{14}O_{14}$) is 1113.5 Da.

6.2.3. sbGnRH-II and -III Purification

Figure 2C:
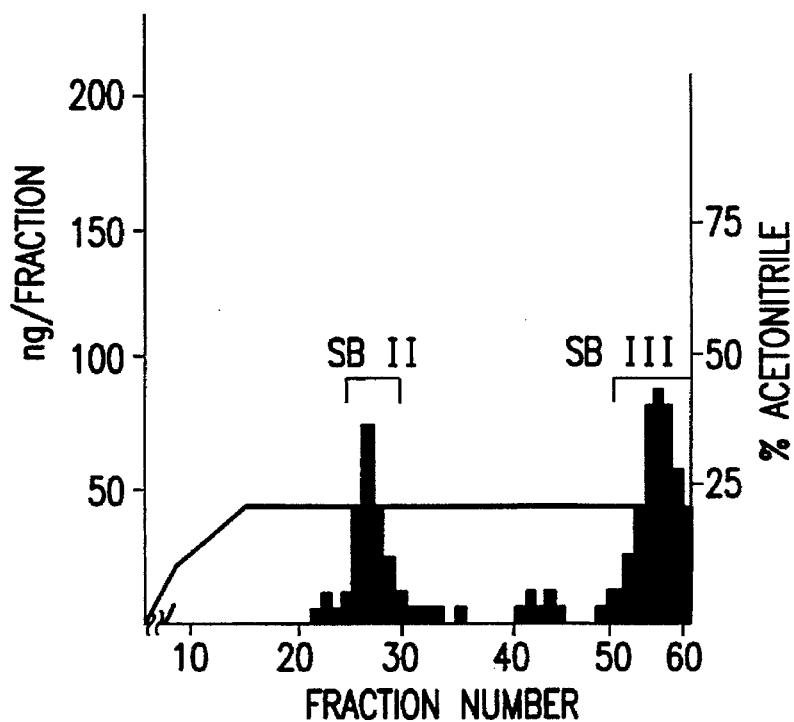

Late-eluting fractions (>50 min) from step 2 of the procedure were assumed to contain two forms of irGnRH as indicated by our preliminary studies in which extracts were compared to synthetic GnRH standards. Likewise, in the present study, irGnRH eluted as two areas in step 3 (FIG. 2C). The earlier-eluting peak was designated sbGnRH-II and was applied to the remaining steps of purification. The later-eluting peak was designated sbGnRH-III and was separately applied to the remaining steps of purification.

TABLE 3

HPLC steps in the purification of sbGnRH-II and -III.

| Step | Solvents: A | Column Type B | | Gradient |
|---|---|---|---|---|
| 3 | 0.25M TEAF | ACN | $C_{18}$ | 17–24% B in 7 min isocratic for 50 min |
| 4 | 0.13M TEAP | ACN | $C_{18}$ | 5–20% B in 10 min, 20–40% B in 40 min |
| 5 | 0.05% TFA | 0.05% TFA in 80% ACN | Phenyl | 5–20% B in 10 min, 20–40% B in 40 min |

6.2.4 Identification of sbGnRH-II

Purification of sbGnRH-II and subsequent protein sequencing and mass spectrometry showed that sbGnRH-II is identical in sequence and mass with cGnRH-II. The amino acid sequence of the pyroglutamate amino peptidase treated sbGnRH-II was determined to be:

His-Trp-Ser-His-Gly-Trp-Tyr-Pro-Gly (SEQ ID NO: 9).

The molecule ion mass of this peptide was m/z 1236.6 (MALDI). The calculated monoisotopic mass (MH$^+$) for pGlu-His-Trp-Ser-His-Gly-Trp-Tyr-Pro-Gly-NH$_2$ (SEQ ID NO: 16) (elemental composition $C_{60}H_{70}N_{17}O_{13}$) is 1236.53 Da. These data confirm that sbGnRH-II is identical in structure to the previously described cGnRH-II (Miyamoto et al., 1984, *Proc. Natl. Acad. Sci. U.S.A.* 81:3874–3878).

6.2.5 Identification of sbGnRH-III sbGnRH-III shares elution position with sGnRH identified for other perciform fish (Sherwood et. al, 1993, *Regul. Pept.* 46:523–534). The late elution position of sbGnRH-III in step 3, Table 3, (FIG. 2C) is consistent with sGnRH in other species (Sherwood et. al, 1993, supra). Likewise, sbGnRH-III maintained a hydrophobic elution position throughout purification but was not present in sufficient quantity to sequence. Further, during the identification of GnRH forms in the pituitary, irGnRH eluted in the same position with the sGnRH standard (see subsection 6.2.6, below).

6.2.6. Identification of Pituitary GnRH

The dominant form of GnRH in seabream pituitaries eluted at the same time as the sbGnRH standard (FIG. 3). A total of 166 ng irGnRH (antiserum GF-4) was detected in fractions 23–24. Only 0.33 ng irGnRH was detected in fractions 46–47 corresponding to the elution position of sGnRH. irGnRH eluting with the cGnRH-II standard was not detected, although, antiserum cross-reactivity of GF-4 with cGnRH-II is 4%.

The same elution pattern was achieved in the elution of hybrid striped bass pituitary extract (FIG. 10). The peak that eluted in the same position as the sbGnRH standard was approximately 1000 times more abundant than the peak that eluted at the postion of the sGnRH standard. Although the eluted material was not directly sequenced, its elution position strongly suggests that it is the same as sbGnRH. The great abundance of this material in striped bass pituitaries with respect to the other GnRH's strongly suggests that sbGnRH is physiologically relevant in a broad variety of fin fish.

7. EXAMPLE: DETERMINATION OF GONADOTROPIN-RELEASING POTENCIES

7.1 MATERIALS AND METHODS

7.1.1 Peptides

Salmon GnRH, cGnRH-II, sbGnRH, [D-Ala$^6$,Pro$^9$-NEt]-sbGnRH and [D-Arg$^6$,Pro$^9$-NEt]-sbGnRH were synthesized using the solid phase method on a methylbenzhydrylamine resin as described by Rivier et al., 1992, supra, and in Section 6.1.5, supra. [D-Ala$^6$,Pro$^9$-NEt]-mGnRH was purchased from Bachem (Calif., USA).

7.1.2 In vivo experiments:

During the spawning season, 104 female seabream at 2 years of age, weighing 458±104 g, with preovulatory oocytes of 500–600 μm in diameter were selected for experimentation. Oocyte developmental stage was determined by microscopic examination of a freshly removed ovarian biopsy, as previously described (Zohar et al., 1979, *J. Fish Biol.* 15:665–670). The bioactivity of the native forms of GnRH and of the GnRH analogs was studied in three consecutive experiments, carried out on day 1, day 3, and day 8. The first experiment included four groups of eight females. Three groups were injected with 5 μg/kg body weight of either sbGnRH, sGnRH or cGnRH-II. The fourth group was injected with saline. The second experiment included four similar groups, except that the peptides were injected at a dose of 25 μg/kg body weight. The third experiment included five groups, each with eight females. One group was injected with native sbGnRH; two other groups were each injected with an analog of sbGnRH, the [D-Ala$^6$,Pro$^9$-NEt]-sbGnRH and [D-Arg$^6$,Pro$^9$-NEt]-sbGnRH; another group was injected with the analog of the mammalian GnRH, [D-Ala$^6$,Pro$^9$-NEt]-mGnRH; and the last group was injected with saline. All peptides in the third experiment were injected at a dose of 5 μg/kg body weight.

In all experiments, the tested peptides were injected into the dorsal musculature, in a volume of 0.5 ml/kg body weight. Each group of fish was held in a separate 600 liter tank exposed to natural photoperiod conditions and supplied with sea water at 20° C. Fish were bled before the injection of the peptides and at 1.5, 4 and 8 hours post-injection. At each bleeding time, 1 ml of blood was removed from the caudal vessels, using a 1 ml syringe fit with a 21G needle. Prior to injection and bleeding, fish were anesthetized in 0.2 ppt of 2-phenoxy-ethanol. Blood was immediately centrifuged and plasma removed and frozen. Levels of seabream GtH-II in the plasma samples were measured using a homologous and specific radioimmunoassay, as previously described (Zohar et al., 1990, *Aquaculture* 88:189–204). Blood GtH-II levels in the various groups were statistically compared using ANOVA followed by Duncan new multiple range comparison test.

7.2 RESULTS

7.2.1 Gonadotropin-releasing activity of the native peptides

All three forms of GnRH present in seabream brains were found to significantly stimulate GtH-II secretion in reproductively mature seabream females ($P<0.05$ for sbGnRH and $P<0.01$ for sGnRH and cGnRH-II, FIGS. 4 and 5). However, cGnRH-II and sGnRH were significantly more potent than the novel sbGnRH ($P<0.001$). In the lower tested dose of 5 μg/kg body weight, blood GtH-II levels in females treated with sbGnRH tended to be higher than in the control females only at 1.5 hours post-injection (inset, FIG. 4). At the same time, cGnRH-II and sGnRH induced blood GtH-II levels were, respectively, 14.50 and 8.35 times higher than GtH-II levels in the control females (FIG. 4). At 4 hours after injection, while GtH-II levels in the females injected with sbGnRH were not different from control levels, GtH-II levels in the females injected with cGnRH-II and sGnRH were still higher, 6.2 and 2.5 times, respectively, than GtH-II levels in the control females. At 8 hours post-injection, only cGnRH-II injected females had higher GtH-II levels (FIG. 4).

At the 5 μg/kg dose and at the most responsive time after injection (1.5 hr.), cGnRH-II was 8 times more potent than sbGnRH and 1.75 times more potent than sGnRH in inducing GtH-II secretion in female seabream. sGnRH was around 5 times more potent than sbGnRH. The same order of potency, namely cGnRH-II>sGnRH>sbGnRH, was observed when a higher dose, 25 μg/kg body weight of the peptides was injected (FIG. 5). At this dose, all three native forms of GnRH induced more intensive GtH secretion than they did at the lower dose. At the higher dose, sbGnRH induced a significant GtH-II release (4.4 times higher than in controls, $P<0.05$) only at 1.5 hours after injection (inset of FIG. 5). At all three post-injection bleeding times, cGnRH-II induced higher GtH-II secretion than did sGnRH or sbGnRH ($P<0.001$). cGnRH-II resulted in GtH-II levels 31.0 (1.5 hr), 10.9 (4 hr) and 5.5 (8 hr) times higher than GtH-II levels in saline-injected fish. sGnRH induced significant elevation in GtH-II levels ($P<0.001$) only at 1.5 hr (15.8 times) and 4 hr (7.8 times) following the injection. At the higher injected dose and the most responsive time (1.5 hr), cGnRH-II was 7 times more potent than sbGnRH and 2 times more potent than sGnRH in inducing GtH-II secretion in female seabream. sGnRH was 3.5 times more potent than sbGnRH.

7.2.2 Gonadotropin-releasing activity of the sbGnRH analogs

The two tested analogs of sbGnRH, [D-Ala$^6$,Pro$^9$-.NEt ]-sbGnRH and [D-Arg$^6$, Pro$^9$-NEt]-sbGnRH, induced a significantly stronger gonadotropin secretion than did the native sbGnRH (FIG. 6, P<0.01), in terms of both the amplitude and the duration of the GtH-II surge. As in the earlier experiment (FIG. 4), the native sbGnRH did not induce significant release of GtH-II at a dose of 5 μg/kg. At all bleeding times, the two analogs of sbGnRH were equipotent (P>0.01). They induced blood GtH-II levels that were 5 times (1.5 hr) to 2.5 times (8 hr) higher than in sbGnRH-injected females. However, both analogs of sbGnRH were found to be much less potent (P<0.001) in inducing GtH-II release than the analog of the mammalian GnRH, [D-Ala$^6$, Pro$^9$-NEt]-mGnRH (FIG. 6). The mammalian GnRH analog induced GtH-II secretion that was 5–6 times higher than that induced by the two sbGnRH analogs at 1.5 hours, 4–7 times higher at 4 hours, and 2.5–4.5 times higher at 8 hours post-injection. Interestingly, at a dose of 5 μg/kg, the two analogs of sbGnRH induced plasma levels of GtH-II that were in the same range as those induced by the native sGnRH and cGnRH-II (compare inset FIG. 6 to FIG. 4).

8. EXAMPLE: CLONING THE sbGnRH cDNA

8.1 MATERIALS AND METHODS

8.1.1 Oligonucleotides

Oligo dT-adaptor primer, 5'-GACTCGAGTCGACATCGA(dT$_{19}$)-3' (SEQ ID NO: 26), and adaptor-I primer, 5'-CGCTCTAGAGACTCGAGTCGACATCGA-3' were kindly donated by Dr. Jan Bogerd, Utrech U., The Netherlands. Degenerate 5' primer 1–8 I, 5'-CGTCGACCAGCA(CT)TGGTCITATGGI(TC)T(ACGT)TC-3' (SEQ ID NO: 5), degenerate 5' primer 1–8 II, 5'-CGTCGACCAGCA(CT)TGGTCITATGGI(TC)T(ACGT)AG-3' (SEQ ID NO: 6), and the degenerate internal probe 8–13 5'-(AT)(GC)(ACGT)CCTGGIGGIAA(AG)(AC)G-3' (SEQ ID NO: 7), were synthesized by the Biopolymer Laboratory, University of Maryland.

8.1.2 mRNA isolation.

Three spermiating seabream males and three ovulating females were sacrificed and the whole brains were removed and immediately frozen in liquid nitrogen. Total RNA was isolated separately from males and females brains by guanidinium/phenol/chloroform extraction, as previously described (Chomczynski et al., 1987, *Anal. Biochem.* 162:156–159). Poly(A$^+$) rich RNA was separated using streptavidin coated magnetic beads and biotinylated oligo (dT) (PolyATract mRNA magnetic separation kit, Promega, Madison, Wis.). 2 g of brain tissue yielded approximately 12 μg of poly(A$^+$) RNA using these procedures. The poly(A$^+$) RNA was lyophilized and resuspended in water to a final concentration of 0.5 μg/μl.

8.1.3 Reverse transcription and 5'RACE-PCR.

Synthesis of cDNA was conducted in a volume of 20 μl containing 4 μl 5×RT buffer (Promega), 2 mM Na-pyrophosphate, 1 mM each dNTP, 20 units RNasin ribonuclease inhibitor (Promega), 0.5 μg seabream brain poly(A$^+$) RNA, 8 units of AMV reverse transcriptase (Promega) and 30 ng of oligo dT-adaptor primer. The cDNA synthesis mixture was incubated for one hour at 42° C. and one hour at 50° C. and then diluted in 50 μl TE buffer pH 8. A fragment of the seabream GnRH precursor cDNA was amplified based on the principle of 5'-RACE PCR (Frohman, 1990, in PCR Protocols: A Guide to Methods and Applications. Innis et al., eds. Academic Press. New York).

The PCR reaction was carried out in a volume of 50 μl containing 3 μl template cDNA, 5 μl 10x PCR buffer (Promega), 2.5 mM MgCl$_2$, 200 μM each dNTP, 2.5 μl formamide, 1.5 μM of degenerate 5' primer (1–8 I or 1–8 II), 0.25 μM adaptor-1 primer and 1.0 units of Taq DNA polymerase (Promega). The amplification was performed using 12 cycles at 94° C., 45° C. and 72° C. for 1 min. each, followed by 21 cycles at 94° C., 55° C. and 72° C. for 1 min. each, followed by 7 min. of extension at 72° C. Size fractionation of the PCR products through an agarose gel (3.5%) revealed a smear, indicative of a variety of products. The DNA was transferred to a MagnaGraph nylon membrane (MSI) and hybridized with a radiolabelled degenerate oligomer (seabream GnRH 8–13) as a probe. 7 ng of the sbGnRH 8–13 was 5' labeled to a specific activity of 5.6×10$^6$ cpm/ng using T4 polynucleotide kinase (Promega) and [γ$^{32}$P]-ATP (Amersham, Arlington Heights, Ill.). Hybridization conditions were 37° C. for 36 hours in 7 ml hybridization buffer [6×SSC, 0.5% SDS, 5x Denhardt's solution, 100 μg/ml tRNA]. The membrane, was washed with 6×SSC, 0.05% Na-pyrophosphate for one hour at 37° C. and subjected to autoradiography.

8.1.4 Cloning of PCR product

Isolation of the 300 bp band was achieved by separation using electrophoresis in an agarose gel and recovery onto NA45 paper (Schleicher & Schuell). The recovered DNA was phosphorylated at 37° C. for one hour in a volume of 30 μl containing 1 mM ATP and 10 units of T4 polynucleotide kinase (Promega). The DNA was then blunt ended using 2 units of Klenow fragment and ligated to SmaI-cut pBluescript SK(+) plasmid vector (Stratagene, La Jolla, Calif.) using 5 units of T4 ligase (Promega). The recombinant plasmid was transformed and propagated in DH5αE. *coli* cells. Nucleotide sequences of the inserts were determined by the dideoxynucleotide chain termination method (Sanger et al., 1977, *Proc. Natl. Acad. Sci. U.S.A.* 74:5463–5467) in both directions using universal primers.

8.1.5 Screening of cDNA library

Two cDNA libraries were made from seabream male and female brains. Each library was constructed in λ-Uni-ZAP XR vector (Stratagene) from 5 μg poly(A+) RNA according to the manufactures directions. cDNA fragments with EcoRI and XhoI linkers were cloned into EcoRI-XhoI cut vector. Approximately 10$^6$ plaques from each library were screened under high stringency using a fragment of the cloned PCR product as a probe. The probe was labeled with random primers and [α$^{32}$P]-dATP. Hybridization was conducted overnight at 43° C. in 50% formamide, 6×SSPE, 0.1% SDS, 1XDenhardt's solution and 10% dextran sulfate. Washing conditions were as follows: 2×SSC, room temp. for 45 min. followed by a 20 min wash in 0.2×SSC at 65° C. for 20 min. Positive clones were plaque purified to homogeneity by three additional screening cycles. The BlueScript plasmid vector containing the cDNA insert was excised from lambda phage using the filamentous helper phage X-Asist (Stratagene). The excised plasmid containing the sbGnRH cDNA insert between the EcoRI and XhoI sites of Bluescript was identified by DNA sequencing, and named pSBGNRH.

8.2 RESULTS

8.2.1 3'RACE-PCR

A 3'RACE-PCR (Frohman et al., 1990, supra) was performed on seabream brain mRNA to amplify a 3' fragment of the sbGnRH precursor cDNA. First strand cDNA was synthesized using an oligo(dT)-adaptor as a primer, described in Section 8.1.1, above. Subsequent PCR amplification was accomplished using a 3' adaptor primer and either one of the two degenerate 5' primers based on amino acids 1–8 of the sbGnRH decapeptide (FIG. 7). An internal oligomer designed according to amino acids 8–13 was used as a hybridization probe on a Southern blot to identify a 300 bp band from a smear of PCR products. The PCR fragment was isolated, cloned and the nucleotide sequences determined. Sequence analysis of the PCR product revealed that the 5' degenerate primer was followed by the codons for five amino acids (Pro, Gly, Gly, Lys, Arg) common to all known GnRH precursors. Based on this information we have decided to use this PCR product as a probe to screen several seabream brain cDNA libraries to obtain a full-length sbGnRH precursor cDNA.

8.2.2 Characterization of the cDNA encoding sbGnRH.

Two cDNA libraries were constructed from poly(A⁺) RNA isolated from spawning male and female seabream brains. Approximately one million plaque forming units (PFU) were plated from each library and screened with the 300 bp PCR product (excluding the poly A tail). Two identical clones were recovered from each library, and further isolated and purified to homogeneity by three subsequent rounds of plaque purification. The complete nucleotide and deduced amino acid sequences encoded by the sbGnRH cDNA are shown in FIG. 8. Nucleotide sequence analysis revealed that the cDNA encodes a 95 amino acid primary translation product which is composed of the three expected major regions: A 25 amino acid leader sequence; the biologically active sbGnRH followed by a processing site (GKR); and a 57 amino acid associated peptide. The coding sequence is flanked by a 36 nucleotide (nt) long 5' untranslated region and a 39-nt long 3' untranslated region. The translation initiation codon is the ATG located at nt 37–39 rather than any of the repeated ATGs at nt 87–95 because its flanking nucleotides conforms more to the consensus sequence for initiation sites in eukaryotic mRNA (Kozak, 1981, *Nucl. Acids Res.* 9:5233–5255). A stop codon is found at nt 285 and is followed by another stop codon. A typical poly-adenylation signal (AATAAA) is present at nt position 305–310.

9. EXAMPLE: MANIPULATION OF SPAWNING IN SEABREAM

Female fish such as seabream (*Sparus aurata*) reaching final stages of vitellogenesis may receive one of the following treatments of sbGnRHa—an analog of sbGnRH as described in Section 5, above.

1. An intramuscular injection of sbGnRHa in a saline solution (10 µg sbGnRHa/kg body weight which is an acceptable amount for injection);
2. Implantation of a Silastic implant according to Crim et al., 1986, *Aquaculture* 56:139–149, containing sbGnRHa (150 µg GnRHa/fish);
3. Implantation of a biodegradable copolymer of polylacticpolyglycolic acid containing sbGnRHa (150 µg sbGnRHa/fish);
4. Placebo injection of saline (Control).

Before the treatment and at various intervals thereafter, the fish may be bled. After withdrawing a blood sample, the fish may be returned into the water. GtH levels may be determined in the withdrawn blood sample by specific homologous radioimmunoassay.

Additionally, several treated, non-bled females from each treatment group may be kept, each in a separate container, which may be connected to an egg collector, together with two males. The females may be followed for their spawning activity, which may be defined as tens of thousands of fertilized eggs collected per day over a period of more than one week.

The GtH released from those fish receiving sbGnRHa treatment may be compared to that of fish receiving placebo. Similarly, the spawning activity of those fish receiving sbGnRHa treatment may be compared to that of fish receiving placebo. The results of GtH release may be correlated with the spawning results to determine the effect of sbGnRHa treatment on spawning.

The present invention is not limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings. Such modifications are intended to fall within the scope of the appended claims.

---

What is claimed is:

1. A peptide having the formula pGlu-His-Trp-Ser-Tyr-$R_6$-Leu-X-pro-$R_{10}$-NHR (SEQ ID NO: 10) or a nontoxic salt thereof wherein X is selected from the group consisting of Ser, Ala, Thr, Pro, and Gly, $R_6$ is a D-isomer of an α-amino acid selected from the group consisting of Trp, Ala, Phe, Lys, Pro, Met, Leu, Glu, Asn, Arg, Tyr, Cys, His, Chg, Nva, Orn, Thr, Abu, Phg, Ile, Glu, Asp, Nle and Val and wherein $R_{10}$ is Gly or des-$R_{10}$ and R is H or $C_nY_{2n}CY_3$, with Y being H or F and n being 0, 1, 2 or 3, provided that when $R_{10}$ is des-$R_{10}$, n is not 0.

2. A peptide in accordance with claim 1 wherein $R_6$ is D-Ala.

3. A peptide in accordance with claim 1 wherein $R_6$ is D-Arg.

4. A peptide in accordance with claim 1 wherein $R_{10}$ is des-$R_{10}$, Y is H and n is 1.

5. A peptide in accordance with claim 1 wherein $R_6$ is D-Ala and $R_{10}$ is des-$R_{10}$, Y is H and n is 1.

6. A peptide in accordance with claim 1 wherein $R_6$ is D-Arg and $R_{10}$ is des-$R_{10}$, Y is H and n is 1.

7. A peptide having the formula pGlu-His-Trp-Ser-Tyr-$R_6$-Leu-Ser-Pro-$R_{10}$-NHR (SEQ ID NO: 10) or a nontoxic salt thereof wherein $R_6$ is a D-isomer of an α-amino acid selected from the group consisting of Trp, Ala, Phe, Lys, Pro, Met, Leu, Glu, Asn, Arg, Tyr, Cys, His, Chg, Nva, Orn, Thr, Abu, Phg, Ile, Glu, Asp, Nle and Val and wherein $R_{10}$ is Gly or des-$R_{10}$ and R is H or $C_nY_{2n}CY_3$, with Y being H or F and n being 0, 1, 2 or 3, provided that when $R_{10}$ is des-$R_{10}$, n is not 0.

8. A peptide in accordance with claim 7 wherein $R_6$ is D-Ala.

9. A peptide in accordance with claim 7 wherein $R_6$ is D-Arg.

10. A peptide in accordance with claim 7 wherein $R_{10}$ is des-$R_{10}$, Y is H and n is 1.

11. A peptide in accordance with claim 7 wherein $R_6$ is D-Ala and $R_{10}$ is des-$R_{10}$, Y is H and n is 1.

12. A peptide in accordance with claim 7 wherein $R_6$ is D-Arg and $R_{10}$ is des-$R_{10}$, Y is H and n is 1.

13. A peptide having the formula pGlu-His-Trp-Ser-Tyr-Gly-Leu-Ser-Pro-Gly-$NH_2$ (SEQ ID NO: 3) or a nontoxic salt thereof.

14. A precursor sbGnRH polypeptide having the amino acid sequence or SEQ ID NO: 2.

15. A method of promoting the spawning of fish by administering to said fish an effective amount of pGlu-His-Trp-Ser-Tyr-$R_6$-Leu-X-pro-$R_{10}$-NHR (SEQ ID NO: 10) or a nontoxic salt thereof wherein X is selected from the group consisting of Ser, Ala, Thr, Pro, and Gly, $R_6$ is a D-isomer of an α-amino acid selected from the group consisting of Trp, Ala, Phe, Lys, Pro, Met, Leu, Glu, Asn, Arg, Tyr, Cys, His, Chg, Nva, Orn, Thr, Abu, Phg, Ile, Glu, Asp, Nle and Val and wherein $R_{10}$ is Gly or des-$R_{10}$ and R is H or $C_nY_{2n}CY_3$, with Y being H or F and n being 0, 1, 2 or 3, provided that when $R_{10}$ is des-$R_{10}$, n is not 0.

16. A method in accordance with claim 15 wherein said administering is by injection.

17. A method in accordance with claim 15 wherein said administering is implantation.

18. A method in accordance with claim 15 wherein said administering is by dissolving in water wherein the fish are swimming.

19. A method in accordance with claim 15 wherein said administering is orally through feed.

* * * * *